US009656987B2

(12) United States Patent
Kawakami et al.

(10) Patent No.: US 9,656,987 B2
(45) Date of Patent: May 23, 2017

(54) PROCESS FOR PREPARING 3-[(S)-7-BROMO-2-((2-OXOPROPYL)AMINO)-5-PYRIDIN-2-YL-3H-1,4-BENZODIAZEPIN-3-YL]PROPIONIC ACID METHYL ESTER

(71) Applicant: PAION UK LIMITED, Cambridge Cambridgeshire (GB)

(72) Inventors: Yuji Kawakami, Fukui (JP); Tatsushi Murase, Fukui (JP); Daisuke Tanaka, Fukui (JP); Hideyuki Yoshiyama, Fukui (JP); Shinitsu Kuwabe, Fukui (JP)

(73) Assignee: PAION UK LIMITED (GB)

( * ) Notice: Subject to any disclaimer, the term of this patent is extended or adjusted under 35 U.S.C. 154(b) by 0 days.

(21) Appl. No.: 14/772,203

(22) PCT Filed: Mar. 3, 2014

(86) PCT No.: PCT/JP2014/055329
§ 371 (c)(1),
(2) Date: Sep. 2, 2015

(87) PCT Pub. No.: WO2014/136730
PCT Pub. Date: Sep. 12, 2014

(65) Prior Publication Data
US 2016/0009680 A1   Jan. 14, 2016

(30) Foreign Application Priority Data
Mar. 4, 2013   (JP) .................. 2013-041492

(51) Int. Cl.
C07D 243/14 (2006.01)
C07D 401/04 (2006.01)
A61K 31/5517 (2006.01)
C07D 487/04 (2006.01)
B01J 31/02 (2006.01)

(52) U.S. Cl.
CPC ........ *C07D 401/04* (2013.01); *A61K 31/5517* (2013.01); *B01J 31/0235* (2013.01); *C07D 487/04* (2013.01); *B01J 2231/763* (2013.01)

(58) Field of Classification Search
CPC ........................ C07D 243/14; C07D 401/04
USPC ...................... 540/571; 546/268.1
See application file for complete search history.

(56) References Cited

U.S. PATENT DOCUMENTS

| 6,916,923 B2 | 7/2005 | Ding et al. |
| 9,156,842 B2 | 10/2015 | Tilbrook et al. |
| 9,193,730 B2 | 11/2015 | Tilbrook et al. |
| 2011/0294843 A1 | 12/2011 | Seumloeehngen et al. |
| 2014/0080815 A1 | 3/2014 | Wilhelm-Ogunbiyi et al. |
| 2015/0148338 A1 | 5/2015 | Graham et al. |
| 2015/0224114 A1 | 8/2015 | Kondo et al. |
| 2015/0368199 A1 | 12/2015 | Tilbrook et al. |

FOREIGN PATENT DOCUMENTS

| JP | 2002-544266 A | 12/2002 |
| JP | 2008515991 A | 5/2008 |
| JP | 2008526984 A | 7/2008 |
| JP | 2009-542787 A | 12/2009 |
| JP | 2011-153104 A | 8/2011 |
| RU | 2249593 C2 | 4/2005 |
| WO | 00/69836 A1 | 11/2000 |
| WO | 2006044504 A1 | 4/2006 |
| WO | 2006078554 A2 | 7/2006 |
| WO | 2008/007071 A1 | 1/2008 |
| WO | 2008/007081 A1 | 1/2008 |
| WO | 2008147815 A1 | 12/2008 |
| WO | 2009/145323 A1 | 12/2009 |
| WO | 2010/116794 A1 | 10/2010 |
| WO | 2011/032692 A1 | 3/2011 |

OTHER PUBLICATIONS

Jordan, V. C. Nature Reviews: Drug Discovery, 2, 2003, 205.*
Dörwald, F. Zaragoza. Side Reactions in Organic Synthesis: A Guide to Successful Synthesis Design, Weinheim: WILEY-VCH Verlag GmbH & Co. KGaA, 2005, Preface.*
Hayashi M., et al., "Oxidative Conversion of Silyl Enol Ethers to alpha- beta-Unsaturated Ketones Employing Oxoammonium Salts," Organic Letters, vol. 14(1), pp. 154-157 (2012).
Hayashi, M. et al., "9-Azanoradamantane N-Oxyl (Nor-AZADO): A Highly Active Organocatalyst for Alcohol Oxidation," Chem. Pharm. Bull., vol. 59(12), pp. 1570-1573 (2011).
International Search Report, PCT/JP2014/055329, dated Apr. 8, 2014, pp. 5.
Pace, V. et al., First General Route to Substituted a-Arylamino-a'-chloropropan-2-ones by Oxidation of N-Protected Aminohalohydrins: The Importance of Disrupting Hydrogen Bond Networks, Synthesis, vol. 20, pp. 3545-3555 (2010).
Shibuya M., et al., "Oxidation of nitroxyl radicals: electrochemical and computational studies," Tetrahedron Letters, vol. 53(16), pp. 2070-2073 (2012).
Shibuya, M. et al., "2-Azaadamantane N-Oxyl (AZADO): Highly efficient organocatalysts for oxidation of alcohols," Journal of the American Chemical Society, vol. 128, pp. 8412-8413 (2006).
Shibuya, M. et al., "Highly Efficient, Organocatalytic Aerobic Alcohol Oxidation,"Journal of American Chemical Society, vol. 133, pp. 6497-6500 (2011).
Zhao, M. et al., "Oxidation of Primary Alcohols to Carboxylic Acids with Sodium Chlorite Catalyzed by TEMPO and Bleach," Journal of Organic Chemistry, vol. 64, pp. 2564-2566 (1999).

(Continued)

*Primary Examiner* — Douglas M Willis
(74) *Attorney, Agent, or Firm* — Foley & Lardner LLP

(57) ABSTRACT

A process for preparing 3-[(S)-7-bromo-2-(2-oxo-propylamino)-5-pyridin-2-yl-3H-1,4,-benzodiazepin-3-yl]propionic acid methyl ester at a high conversion rate with good reproducibility by oxidizing 3-[(S)-7-bromo-2-(2-hydroxypropylamino)-5-pyridin-2-yl-3H-benzo[e][1,4]diazepin-3-yl]propionic acid methyl ester in the presence of an oxidation catalyst is provided by defining the ammonium ion content of 3-[(S)-7-bromo-2-(2-hydroxy-propylamino)-5-pyridin-2-yl-3H-benzo[e][1,4]diazepin-3-yl]propionic acid methyl ester.

5 Claims, 2 Drawing Sheets

(56) References Cited

OTHER PUBLICATIONS

U.S. Appl. No. 12/373,472, filed Nov. 2, 2009, Gary Stuart Tilbrook.
U.S. Appl. No. 13/496,742, filed Aug. 30, 2012, Gary Stuart Tilbrook.
U.S. Appl. No. 13/883,935, filed Sep. 10, 2013, Karin Wilhelm-Ogunbiyi.
U.S. Appl. No. 14/746,026, filed Jun. 22, 2015, Gary Stuart Tilbrook.
U.S. Appl. No. 14/402,590, filed Nov. 20, 2014, John Aitken Graham.
U.S. Appl. No. 14/948,889, filed Nov. 23, 2015, Gary Stuart Tilbrook.
U.S. Appl. No. 14/841,899, filed Sep. 1, 2015, Gary Stuart Tilbrook.
U.S. Appl. No. 14/424,340, filed Feb. 26, 2015, Maki Kondo.

\* cited by examiner

PROCESS FOR PREPARING 3-[(S)-7-BROMO-2-((2-OXOPROPYL)AMINO)-5-PYRIDIN-2-YL-3H-1,4-BENZODIAZEPIN-3-YL]PROPIONIC ACID METHYL ESTER

CROSS-REFERENCE TO RELATED APPLICATIONS

This application is a 35 U.S.C. 371 national stage filing of International Application No. PCT/JP2014/055329, filed on Mar. 3, 2014, which claims priority to Japanese Patent Application No. 2013-041492, filed on Mar. 4, 2013. The contents of the aforementioned applications are hereby incorporated by reference in their entireties.

FIELD OF THE INVENTION

The present invention relates to a process for preparing 3-[(S)-7-bromo-2-(2-oxo-propylamino)-5-pyridin-2-yl-3H-1,4-benzodiazepin-3-yl]propionic acid methyl ester by subjecting, to an oxidation reaction, a compound selected from the group consisting of 3-[(S)-7-bromo-2-(2-hydroxy-propylamino)-5-pyridin-2-yl-3H-benzo[1,4]diazepin-3-yl]propionic acid methyl ester, 3-[(S)-7-bromo-2-((R)-2-hydroxy-propylamino)-5-pyridin-2-yl-3H-benzo[e][1,4]diazepin-3-yl]propionic acid methyl ester, and 3-[(S)-7-bromo-2-((S)-2-hydroxy-propylamino)-5-pyridin-2-yl-3H-benzo[e][1,4]diazepin-3-yl]propionic acid methyl ester.

More specifically, the present invention relates to a novel preparation process capable of providing 3-[(S)-7-bromo-2-(2-oxo-propylamino)-5-pyridin-2-yl-3H-1,4-benzodiazepin-3-yl]propionic acid methyl ester at a high conversion rate (reaction efficiency) with good reproducibility even when an oxidation reaction is conducted using, as a raw material, a compound selected from the group consisting of 3-[(S)-7-bromo-2-(2-hydroxy-propylamino)-5-pyridin-2-yl-3H-benzo[e][1,4]diazepin-3-yl]propionic acid methyl ester, 3-[(S)-7-bromo-2-((R)-2-hydroxy-propylamino)-5-pyridin-2-yl-3H-benzo[e][1,4]diazepin-3-yl]propionic acid methyl ester, and 3-[(S)-7-bromo-2-((S)-2-hydroxy-propylamino)-5-pyridin-2-yl-3H-benzo[e][1,4]diazepin-3-yl]propionic acid methyl ester which are each an unpurified compound.

BACKGROUND OF THE INVENTION

Each reaction step for preparing an active pharmaceutical ingredient should be a step that proceeds with a good reaction yield, is conducted with good reproducibility, can provide a high-purity product, and is thus suited for industrial production. Impurities which have appeared in each preparation process can be removed in a purification step, but a preparation process having such a purification step is not always a process suited for industrial production, because the purification step makes the work cumbersome and reduces a working efficiency. Moreover, an increase in the frequency of the purification step may reduce a total yield of a desired active pharmaceutical ingredient. There is therefore a demand for the establishment of a preparation process in which the number of purification steps is reduced as much as possible and which, as described above, proceeds with a good reaction yield, provides a high-purity product with good reproducibility, and is to thus suited for industrial production.

3-[(4S)-8-bromo-1-methyl-6-(2-pyridinyl)-4H-imidazo[1,2,-a][1,4]benzodiazepin-4-yl]propionic acid methyl ester benzenesulfonate is a compound having sedative and anesthetic actions.

Patent Document 1 describes a process for preparing 3-[(S)-7-bromo-2-(2-oxo-propylamino)-5-pyridin-2-yl-3H-1,4-benzodiazepin-3-yl]propionic acid methyl ester by subjecting 3-[(S)-7-bromo-2-((R)-2-hydroxy-propylamino)-5-pyridin-2-yl-3H-benzo[e][1,4]-diazepin-3-yl]propionic acid methyl ester purified by recrystallization to Dess-Martin (Dess-Martin periodinane) oxidation or TEMPO (2,2,6,6-tetramethylpiperidin-N-oxyl) oxidation.

The Dess-Martin oxidation or TEMPO oxidation used in the above process is a well-known process for converting a secondary alcohol compound into a corresponding ketone compound (Non-patent Documents 1 to 4). Although Dess-Martin oxidation is capable of oxidizing a secondary alcohol compound under mild conditions, it is not completely suited for the industrial level production, because as is already known, the reagent itself is potentially explosive. On the other hand, it is said that TEMPO oxidation can be conducted under mild conditions and is an oxidation reaction ordinarily usable in the industrial level production. It has however been pointed out that TEMPO oxidation of an aromatic ring-containing compound causes chlorination of the aromatic ring as a side reaction and this problem may lead to a reduction in yield of a target compound in TEMPO oxidation (refer to Non-patent Document 5).

Thus, there is not known a industrially suited process for preparing 3-[(S)-7-bromo-2-(2-oxo-propylamino)-5-pyridin-2-yl-3H-1,4-benzodiazepin-3-yl]propionic acid methyl ester which is a synthesis intermediate of 3-[(4S)-8-bromo-1-methyl-6-(2-pyridinyl)-4H-imidazo[1,2-a][1,4]benzodiazepin-4-yl]propionic acid methyl ester benzenesulfonate by oxidizing 3-[(S)-7-bromo-2-(2-hydroxy-propylamino)-5-pyridin-2-yl-3H-benzo[e][1,4]diazepin-3-yl]propionic acid methyl ester, which is a raw material compound of the intended compound, safely with a high efficiency.

CITED REFERENCES

Patent Document

Patent Document 1: WO 2011/032692

Non-Patent Documents

Non-patent Document 1: Journal of the American Chemical Society, 128, 8412-8413 (2006)
Non-patent Document 2: Journal of the American Chemical Society, 133, 6497-6500 (2011)
Non-patent Document 3: Chemical & Pharmaceutical Bulletin, 59, 1570-1573 (2011)
Non-patent Document 4: Synthesis, 20, 3545-3555 (2010)
Non-patent Document 5: Journal of Organic Chemistry, 64, 2564-2566 (1999)

BRIEF SUMMARY OF THE INVENTION

The present inventors have studied, by using various oxidation catalysts, the safety and reaction efficiency of an oxidation method of 3-[(S)-7-bromo-2-(2-hydroxy-propylamino)-5-pyridin-2-yl-3H-benzo[e][1,4]diazepin-3-yl]propionic acid methyl ester (which may hereinafter be abbreviated as "Compound (EM)") for safely and efficiently obtaining 3-[(S)-7-bromo-2-(2-oxo-propylamino)-5-pyridin-2-yl-3H-1,4-benzodiazepin-3-yl]propionic acid methyl ester (which may hereinafter be abbreviated as "Compound (FK)") which is a synthesis intermediate of 3-[(4S)-8-bromo-1-methyl-6-(2-pyridinyl)-4H-imidazo[1,2-a][1,4]-benzodiazepin-4-yl]propionic acid methyl ester benzenesulfonate (which may hereinafter be abbreviated as "Compound (P)") having sedative and anesthetic actions. The study suggested that a good result can be obtained by using AZADO (2-azaadamantane-N-oxyl) that similar to TEMPO, belongs to N-oxyl oxidation catalysts. It has however been revealed that when an oxidation reaction using AZADO is repeated, reproducibility of a conversion rate (reaction efficiency) cannot be achieved for some reasons in spite of the reaction repeated under the same conditions.

In short, an object of the present invention is to find a reason why reproducibility of a conversion rate (reaction efficiency) cannot be achieved in an oxidation reaction using AZADO and establish an oxidation method of Compound (EM) which is capable of preparing Compound (FK) at a high conversion rate (reaction efficiency) with good reproducibility, safe, highly efficient, and applicable to industrial production.

With a view to achieving the above-mentioned object, the present inventors have extensively studied the reason why the reproducibility of a conversion rate (reaction efficiency) was not achieved in an oxidation reaction using AZADO. As a result, it has been found that a slight amount of an ammonium ion mixed in the reaction system impedes the oxidation reaction. The study has been made further to find that an oxidation reaction is conducted at a high conversion rate (reaction efficiency) with excellent reproducibility by reducing the amount of an ammonium ion present in the reaction system to a certain amount or less; that reduction of the amount of an ammonium ion can be applied not only to oxidation reactions using AZADO but also to general oxidation reactions using AZADO analogs; and that this reduction can be applied even to general oxidation reactions using N-oxyl oxidation catalysts including TEMPO, leading to the completion of the present invention.

Described specifically, the present invention relates to:

[1] a process for preparing 3-[(S)-7-bromo-2-(2-oxo-propylamino)-5-pyridin-2-yl-3H-1,4-benzodiazepin-3-yl]propionic acid methyl ester (Compound (FK)) by subjecting, to an oxidation reaction, a compound selected from the group consisting of 3-[(S)-7-bromo-2-(2-hydroxy-propylamino)-5-pyridin-2-yl-3H-benzo[e][1,4]diazepin-3-yl]propionic acid methyl ester ("Compound (EM)"), 3-[(S)-7-bromo-2-((R)-2-hydroxy-propylamino)-5-pyridin-2-yl-3H-benzo[e][1,4]diazepin-3-yl]propionic acid methyl ester (which may hereinafter be abbreviated as "Compound (E)"), and 3-[(S)-7-bromo-2-((S)-2-hydroxy-propylamino)-5-pyridin-2-yl-3H-benzo[e][1,4]diazepin-3-yl]propionic acid methyl ester (which may hereinafter be abbreviated as "Compound (E')") in the presence of at least one oxidation catalyst selected from the group consisting of a compound represented by the following formula (I-1), (I-2) or (I-3):

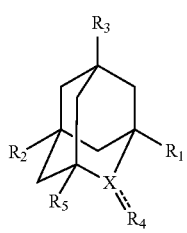
(I-1)

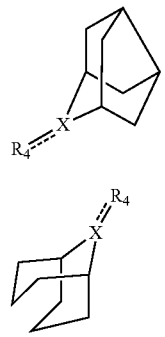
(I-2)

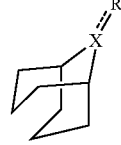
(I-3)

(wherein, $R_1$, $R_2$, and $R_5$ each independently represent a hydrogen atom, a halogen, a hydroxyl group, a $C_{1-3}$ alkyl group, or a $C_{1-3}$ alkoxy group, $R_3$ represents a hydrogen atom or a halogen, and

represents N—O., N—OH, or $N^+$=O), 2,2,6,6-tetramethylpiperidin-N-oxyl, 2,2,6,6-tetramethylpiperidin-1-ol, 4-hydroxy-2,2,6,6-tetramethylpiperidin-N-oxyl, and 2,2,6,6-tetramethyl-1,4-piperidinediol, salts thereof, and solvates thereof, wherein the oxidation reaction is conducted in a reaction system satisfying at least one of the following conditions (a) to (c):

(a) in the absence of an ammonium ion, (b) in the presence of an ammonium ion in a weight ratio of 170 ppm or less relative to the compound selected from the group consisting of Compound (EM), Compound (E), and Compound (E') as a compound to be subjected to the oxidation reaction, and (c) in the presence of an ammonium ion in a molar ratio of 145% or less relative to the oxidation catalyst;

[2] the preparation process as described above in [1], wherein the compound selected from the group consisting of Compound (EM), Compound (E), and Compound (E') is an unpurified compound;

[3] the preparation process as described above in [1] or [2], wherein the oxidation reaction is conducted at a conversion rate of 98% or more;

[4] the preparation process as described above in any one of [1] to [3], wherein Compound (EM) is obtained by conducting an addition reaction between 3-[(S)-7-bromo-2-oxo-5-pyridin-2-yl-2,3-dihydro-1H-1,4-benzodiazepin-3-yl]propionic acid methyl ester (which may hereinafter be abbreviated as "Compound (D)") and 1-aminopropan-2-ol, followed by washing;

[5] the preparation process as described above in any one of [1] to [3], wherein Compound (E) is obtained by conducting an addition reaction between Compound (D) and (R)-1-aminopropan-2-ol, followed by washing;

[6] the preparation process as described above in any one of [1] to [3], wherein Compound (E') is obtained by conducting an addition reaction between Compound (D) and (S)-1-aminopropan-2-ol, followed by washing;

[7] the preparation process as described above in any one of [4] to [6], wherein washing is conducted with a water soluble solution having a pH of from about 3.5 to about 10.5;

[8] the preparation process as described above in [7], wherein the water soluble solution is an aqueous solution of ammonium chloride, an aqueous solution of sodium monohydrogen phosphate, an aqueous solution of sodium dihydrogen phosphate, and/or a phosphate buffer;

[9] the preparation process as described above in any one of [1] to [8], wherein the oxidation catalyst is either 2-azaadamantane-N-oxyl or 2-azaadamantan-2-ol;

[10] a process for preparing Compound (FK) by subjecting Compound (E) to an oxidation reaction in the presence of an oxidation catalyst which is either 2-azaadamantane-N-oxyl or 2-azaadamantan-2-ol, wherein the Compound (E) is a compound obtained by conducting an addition reaction between Compound (D) and (R)-1-aminopropan-2-ol, followed by washing with a phosphate buffer;

[11] the preparation process as described above in [10], wherein Compound (E) is an unpurified compound;

[12] Compound (FK), obtained by subjecting a compound selected from the group consisting of Compound (EM), Compound (E), and Compound (E') to an oxidation reaction in the presence of at least one oxidation catalyst selected from the group consisting of a compound represented by the following formula (I-1), (I-2) or (I-3):

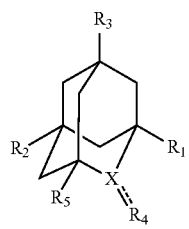
(I-1)

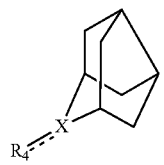
(I-2)

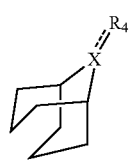
(I-3)

(wherein, all the symbols have the same meanings as described above in [1]), 2,2,6,6-tetramethylpiperidin-N-oxyl, 2,2,6,6-tetramethylpiperidin-1-ol, 4-hydroxy-2,2,6,6-tetramethylpiperidin-N-oxyl, and 2,2,6,6-tetramethyl-1,4-piperidinediol, salts thereof, and solvates thereof, wherein the oxidation reaction is conducted in a reaction system satisfying at least one of the following conditions (a) to (c):

(a) in the absence of an ammonium ion,
(b) in the presence of an ammonium ion in a weight ratio of 170 ppm or less relative to the compound selected from the group consisting of Compound (EM), Compound (E), and Compound (E') as a compound to be subjected to the oxidation reaction, and
(c) in the presence of an ammonium ion in a molar ratio of 145% or less relative to the oxidation catalyst;

[13] Compound (FK) as described above in [12], wherein the compound selected from the group consisting of Compound (EM), Compound (E), and Compound (E') is an unpurified compound;

[14] Compound (FK) as describe above in [12] or [13], wherein the oxidation reaction is conducted at a conversion rate of 98% or more;

[15] Compound (FK) as described above in any one of [12] to [14], wherein Compound (EM) is obtained by conducting an addition reaction between Compound (D) and 1-aminopropan-2-ol, followed by washing;

[16] Compound (FK) as described above in any one of [12] to [14], wherein Compound (E) is obtained by conducting an addition reaction between Compound (D) and (R)-1-aminopropan-2-ol, followed by washing;

[17] Compound (FK) as described above in any one of [12] to [14], wherein Compound (E') is obtained by conducting an addition reaction between Compound (D) and (S)-1-aminopropan-2-ol, followed by washing;

[18] Compound (FK) as described above in any one of [15] to [17], wherein washing is conducted with a water soluble solution having a pH of from about 3.5 to about 10.5;

[19] Compound (FK) as described above in [18], wherein the water soluble solution is an aqueous solution of ammonium chloride, an aqueous solution of sodium monohydrogen phosphate, an aqueous solution of sodium dihydrogen phosphate, and/or a phosphate buffer;

[20] Compound (FK) as described above in any one of [12] to [19], wherein the oxidation catalyst is either 2-azaadamantane-N-oxyl or 2-azaadamantan-2-ol;

[21] 3-[(4S)-8-bromo-1-methyl-6-(2-pyridinyl)-4H-imidazo[1,2-a][1,4]benzodiazepin-4-yl]propionic acid methyl ester benzenesulfonate (Compound (P)), obtained by the following steps (i) to (iii):

(i) a step of conducting an addition reaction between Compound (D) and (R)-1-aminopropan-2-ol and then washing with a phosphate buffer to obtain Compound (E);

(ii) a step of subjecting Compound (E) obtained in the step (i) to an oxidation reaction in the presence of an oxidation catalyst which is either 2-azaadamantane-N-oxyl or 2-azaadamantan-2-ol to obtain Compound (FK); and (iii) a step of reacting Compound (FK) obtained in the step (ii) with benzenesulfonic acid to obtain Compound (P);

[22] Compound (P) as described above in [21], wherein Compound (E) is an unpurified compound;

[23] a reaction composition containing a compound selected from the group consisting of Compound (EM), Compound (E), and Compound (E'), an oxidizing agent, an oxidation catalyst, and a solvent, which contains no ammonium ion or contains an ammonium ion in a weight ratio of 170 ppm or less relative to the compound selected from the group consisting of Compound (EM), Compound (E), and Compound (E') as the compound to be subjected to the oxidation reaction or in a molar ratio of 145% or less relative to the oxidation catalyst;

[24] the reaction composition as described above in [23], for the preparation of Compound (FK);

[25] the reaction composition as described above in [23] or [24], wherein the oxidation catalyst is selected from the group consisting of a compound represented by the following formula (I-1), (I-2) or (I-3):

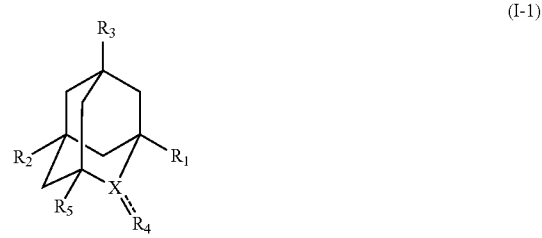
(I-1)

-continued (I-2)

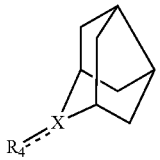

(I-3)

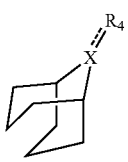

(wherein, all the symbols have the same meanings as described above in [1]), 2,2,6,6-tetramethylpiperidin-N-oxyl, 2,2,6,6-tetramethylpiperidin-1-ol, 4-hydroxy-2,2,6,6-tetramethylpiperidin-N-oxyl, and 2,2,6,6-tetramethyl-1,4-piperidinediol, salts thereof, and solvates thereof.

According to the present invention, Compound (FK) can be prepared from a compound selected from the group consisting of Compound (EM), Compound (E), and Compound (E'), even if the compound is an unpurified compound, at a markedly high conversion rate and/or oxidation catalyst efficiency with good reproducibility. Described specifically, Compound (FK) can be prepared with good reproducibility and high efficiency by using as a starting material Compound (EM) whose ammonium ion remaining content has been defined and subjecting it to an oxidation reaction while using TEMPO, 2-azaadamantane-N-oxyl (which may hereinafter be abbreviated as "AZADO") or an analog thereof, which will be described later as an oxidation catalyst. This Compound (FK) is an important synthesis intermediate of Compound (P) having both sedative and anesthetic actions. Since the preparation process of the present invention can stably supply Compound (FK) safely and with good reproducibility without conducting a particular purification step, it is very useful from the standpoint of industrial productivity of Compound (P) which is an active pharmaceutical ingredient.

DETAILED DESCRIPTION OF THE INVENTION

Figure 1:
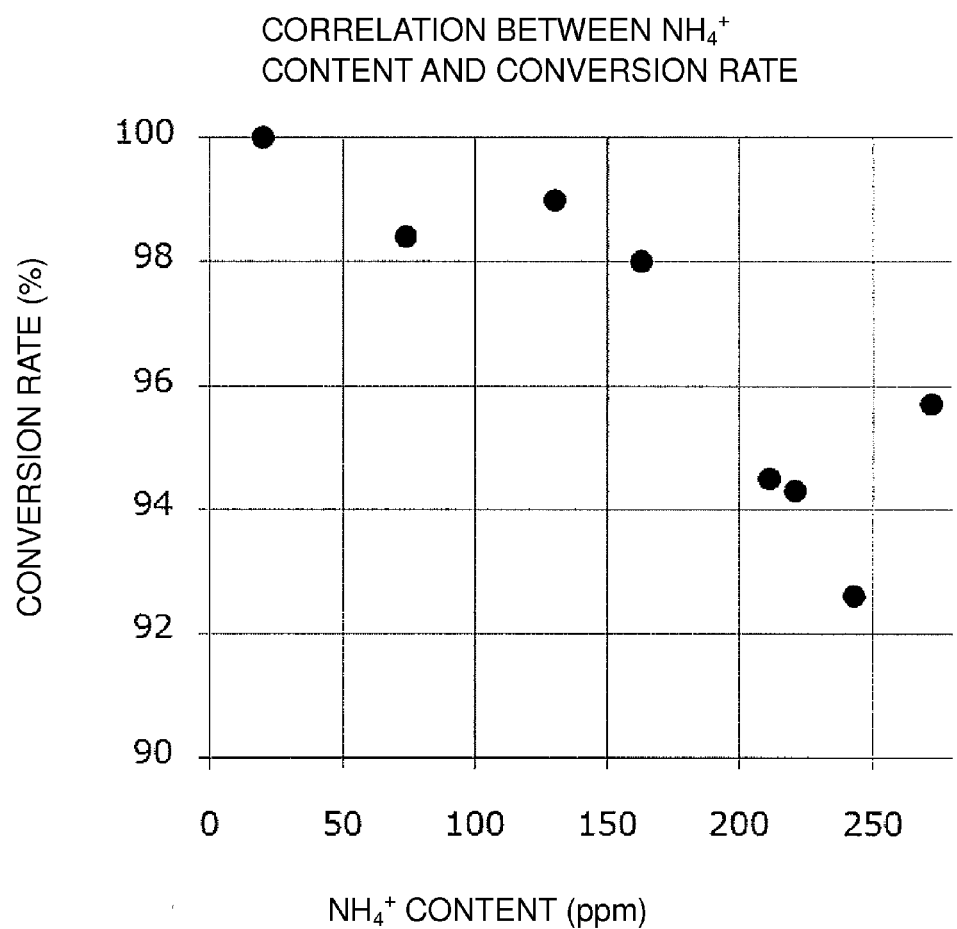
FIG. 1 is a graph plotting an ammonium ion content and a conversion rate from Compound (E) to Compound (FK) in the present invention.

The present invention will hereinafter be described in detail.

In the present invention, "3-[(4S)-8-bromo-1-methyl-6-(2-pyridinyl)-4H-imidazo[1,2-a][1,4]-benzodiazepin-4-yl] propionic acid methyl ester benzenesulfonate (Compound (P))" is a compound having a structure represented by the following formula:

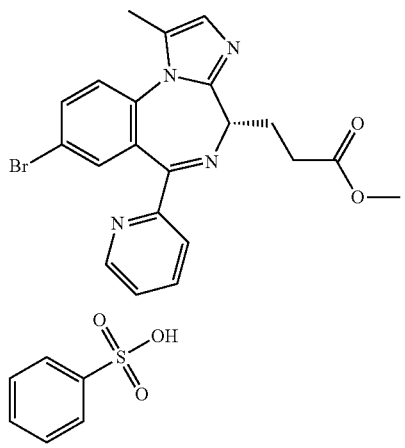

In the present invention, "3-[(S)-7-bromo-2-(2-oxo-propylamino)-5-pyridin-2-yl-3H-1,4-benzodiazepin-3-yl]propionic acid methyl ester (Compound (FK))" is a compound having a structure represented by the following formula:

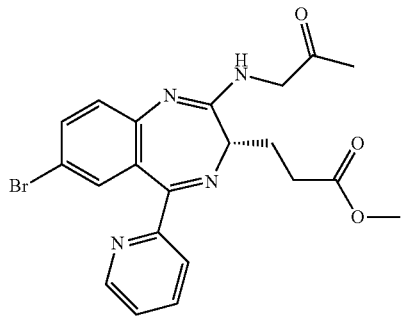 [SMILES: COC(=O)CC[C@@H]1N=C(c2ccccn2)c2cc(Br)ccc2N=C1NCC(C)=O]

In the present invention, "3-[(S)-7-bromo-2-(2-hydroxy-propylamino)-5-pyridin-2-yl-3H-benzo[e][1,4]diazepin-3-yl]propionic acid methyl ester (Compound (EM))" is a compound having a structure represented by the following formula:

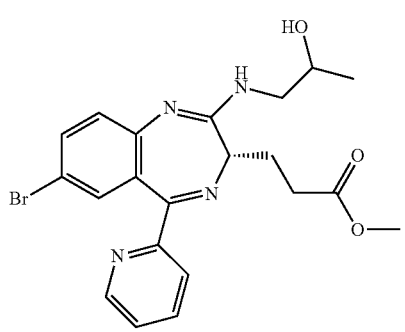 [SMILES: COC(=O)CC[C@@H]1N=C(c2ccccn2)c2cc(Br)ccc2N=C1NCC(C)O]

and is a mixture having, at any ratio, Compound (E) and Compound (E') which will be described later.

In the present invention, "3-[(S)-7-bromo-2-((R)-2-hydroxy-propylamino)-5-pyridin-2-yl-3H-benzo[e][1,4]diazepin-3-yl]propionic acid methyl ester (Compound (E))" is a compound having a structure represented by the following formula:

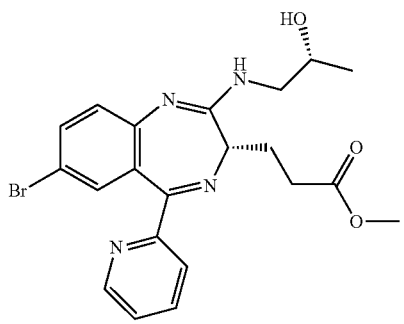 [SMILES: COC(=O)CC[C@@H]1N=C(c2ccccn2)c2cc(Br)ccc2N=C1NC[C@@H](C)O]

In the present invention, "3-[(S)-7-bromo-2-((S)-2-hydroxy-propylamino)-5-pyridin-2-yl-3H-benzo[e][1,4]diazepin-3-yl]propionic acid methyl ester (Compound (E'))" is a compound having a structure represented by the following formula:

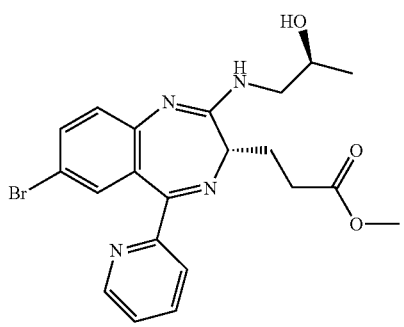 [SMILES: COC(=O)CC[C@@H]1N=C(c2ccccn2)c2cc(Br)ccc2N=C1NC[C@H](C)O]

In the present invention, "3-[(S)-7-bromo-2-oxo-5-pyridin-2-yl-2,3-dihydro-1H-1,4-benzodiazepin-3-yl]propionic acid methyl ester (Compound (D))" is a compound having a structure represented by the following formula:

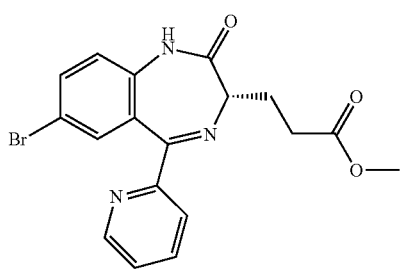 [SMILES: COC(=O)CC[C@@H]1N=C(c2ccccn2)c2cc(Br)ccc2NC1=O]

In the present invention, the term "halogen" means fluorine, chlorine, bromine, or iodine. In the present invention, the term "$C_{1-3}$ alkyl group" means methyl, ethyl, n-propyl, or isopropyl.

In the present invention, the term "$C_{1-3}$ alkoxy group" means methoxy, ethoxy, n-propoxy, or isopropoxy.

In the present invention, examples of the compound represented by the formula (I-1) include AZADO (another name: 2-azatricyclo[3.3.1.1$^{3,7}$]dec-2-yloxidanyl):

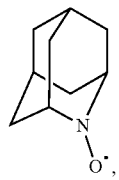

2-azaadamantane-N-oxoammonium cation (another name: 2-oxo-2-azoniatricyclo[3.3.1.1$^{3,7}$]decane) (which may hereinafter be abbreviated as "AZADO cation"):

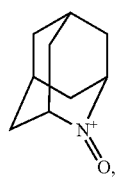

2-azaadamantan-2-ol (another name: 2-azatricyclo[3.3.1.1$^{3,7}$]decan-2-ol) (which may hereinafter be abbreviated as "AZADOH"):

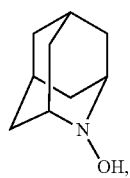

1-methyl-2-azaadamantan-N-oxyl (another name: (1-methyl-2-azatricyclo[3.3.1.1$^{3,7}$]dec-2-yl)oxidanyl) (which may hereinafter be abbreviated as "Me-AZADO"):

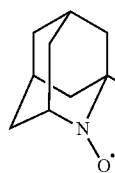

1-methyl-2-azaadamantane-N-oxoammonium cation (another name: 1-methyl-2-oxo-2-azoniatricyclo[3.3.1.1$^{3,7}$]decane) (which may hereinafter be abbreviated as "Me-AZADO cation"):

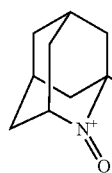

1-methyl-2-azaadamantan-2-ol (another name: 1-methyl-2-azatricyclo[3.3.1.1$^{3,7}$]decan-2-ol) (which may hereinafter be abbreviated as "Me-AZADOH):

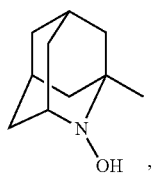

5-hydroxy-1-methyl-2-azaadamantane-N-oxyl (another name: (5-hydroxy-1-methyl-2-azatricyclo[3.3.1.1[3,7]]dec-2-yl)oxidanyl) (which may hereinafter be abbreviated as "5-OH-1-Me-AZADO"):

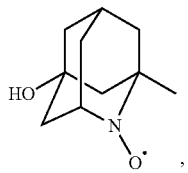

5-hydroxy-1-methyl-2-azaadamantane-N-oxoammonium cation (another name: 5-hydroxy-1-methyl-2-oxo-2-azoniatricyclo[3.3.1.1[3,7]]decane) (which may hereinafter be abbreviated as "5-OH-1-Me-AZADO cation"):

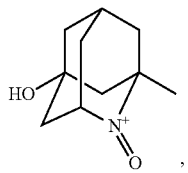

5-hydroxy-1-methyl-2-azaadamantan-2-ol (another name: 1-methyl-2-azatricyclo[3.3.1.1[3,7]]decane-2,5-diol) (which may hereinafter be abbreviated as "5-OH-1-Me-AZADOH"):

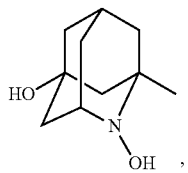

5-methoxy-1-methyl-2-azaadamantane-N-oxyl (another name: (5-methoxy-1-methyl-2-azatricyclo[3.3.1.1[3,7]]dec-2-yl)oxidanyl) (which may hereinafter be abbreviated as "5-MeO-1-Me-AZADO"):

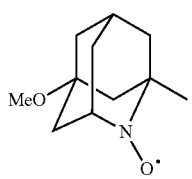

5-methoxy-1-methyl-2-azaadamantane-N-oxoammonium cation (another name: (5-methoxy-1-methyl-2-oxo-2-azoniatricyclo[3.3.1.1[3,7]]decane) (which may hereinafter be abbreviated as "5-MeO-1-Me-AZADO cation"):

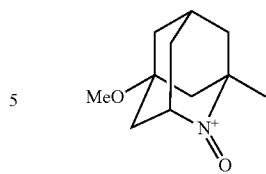

5-methoxy-1-methyl-2-azaadamantan-2-ol (another name: (5-methoxy-1-methyl-2-azatricyclo[3.3.1.1[3,7]]decan-2-ol) (which may hereinafter be abbreviated as "5-MeO-1-Me-AZADOH"):

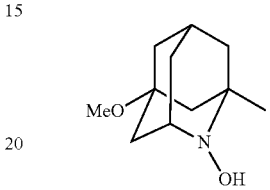

5-fluoro-1-methyl-2-azaadamantane-N-oxyl (another name: (5-fluoro-1-methyl-2-azatricyclo[3.3.1.1[3,7]]dec-2-yl)oxidanyl) (which may hereinafter be abbreviated as "5-F-1-Me-AZADO"):

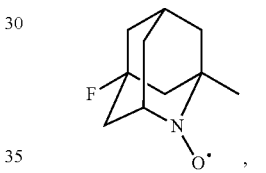

5-fluoro-1-methyl-2-azaadamantane-N-oxoammonium cation (another name: (5-fluoro-1-methyl-2-oxo-2-azoniatricyclo[3.3.1.1[3,7]]decane) (which may hereinafter be abbreviated as "5-F-1-Me-AZADO cation):

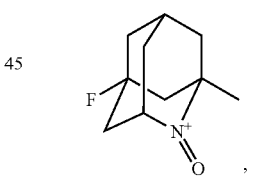

5-fluoro-1-methyl-2-azaadamantan-2-ol (another name: 5-fluoro-1-methyl-2-azatricyclo[3.3.1.1[3,7]]decan-2-ol) (which may hereinafter be abbreviated as "5-F-1-Me-AZADOH"):

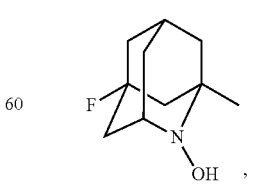

1-fluoro-2-azaadamantane-N-oxyl (another name: (1-fluoro-2-azatricyclo[3.3.1.1[3,7]]dec-2-yl)oxidanyl) (which may hereinafter be abbreviated as "1-F-AZADO"):

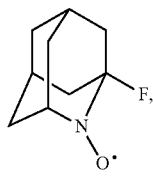

1-fluoro-2-azaadamantane-N-oxoammonium cation (another name: 1-fluoro-2-oxo-azoniatricyclo[3.3.1.1$^{3,7}$]decane) (which may hereinafter be abbreviated as "1-F-AZADO cation"):

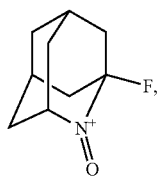 [SMILES: O=[N+]1C2CC3CC(C2)CC1(F)C3]

1-fluoro-2-azaadamantan-2-ol (another name: 1-fluoro-2-azatricyclo[3.3.1.1$^{3,7}$]decan-2-ol) (which may hereinafter be abbreviated as "1-F-AZADOH"):

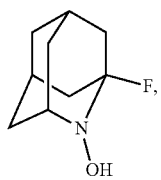 [SMILES: ON1C2CC3CC(C2)CC1(F)C3]

5-fluoro-2-azaadamantane-N-oxyl (another name: (5-fluoro-2-azatricyclo[3.3.1.1$^{3,7}$]dec-2-yl)oxidanyl) (which may hereinafter be abbreviated as "5-F-AZADO"):

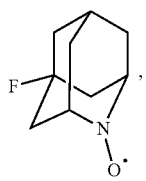

5-fluoro-2-azaadamantane-N-oxoammonium cation (another name: 5-fluoro-2-oxo-azoniatricyclo[3.3.1.1$^{3,7}$]decane) (which may hereinafter be abbreviated as "5-F-AZADO cation"):

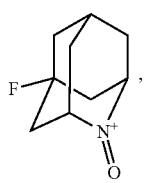

5-fluoro-2-azaadamantan-2-ol (another name: 5-fluoro-2-azatricyclo[3.3.1.1$^{3,7}$]decan-2-ol) (which may hereinafter be abbreviated as "5-F-AZADOH"):

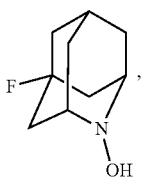

5,7-difluoro-1-methyl-2-azaadamantane-N-oxyl (another name: (5,7-difluoro-1-methyl-2-azatricyclo[3.3.1.1$^{3,7}$]dec-2-yl)oxidanyl) (which may hereinafter be abbreviated as "5,7-diF-1-Me-AZADO"):

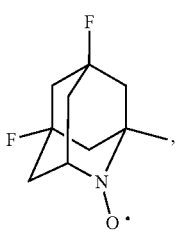

5,7-difluoro-1-methyl-2-azaadamantane-N-oxoammonium cation (another name: (5,7-difluoro-1-methyl-2-oxo-2-azoniatricyclo[3.3.1.1$^{3,7}$]decane) (which may hereinafter be abbreviated as "5,7-diF-1-Me-AZADO cation"):

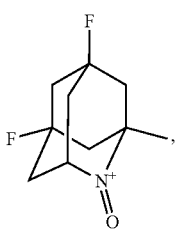

5,7-difluoro-1-methyl-2-azaadamantan-2-ol (another name: 5,7-difluoro-1-methyl-2-azatricyclo[3.3.1.1$^{3,7}$]decan-2-ol) (which may hereinafter be abbreviated as "5,7-diF-1-Me-AZADOH):

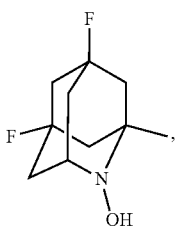

1,3-dimethyl-2-azaadamantane-N-oxyl (another name: (1,3-dimethyl-2-azatricyclo[3.3.1.1$^{3,7}$]dec-2-yl)oxidanyl) (which may hereinafter be abbreviated as "1,3-diMe-AZADO"):

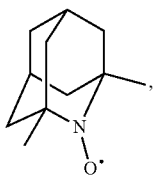

1,3-dimethyl-2-azaadamantane-N-oxoammonium cation (another name: 1,3-dimethyl-2-oxo-2-azoniatricyclo[3.3.1.1$^{3,7}$]decane) (which may hereinafter be abbreviated as "1,3-diMe-AZADO cation):

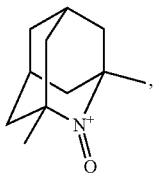

and 1,3-dimethyl-2-azaadamantan-2-ol (another name: 1,3-dimethyl-2-azatricyclo[3.3.1.1$^{3,7}$]decan-2-ol) (which may hereinafter be abbreviated as "1,3-diMe-AZADOH"):

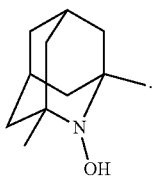

In the present invention, the compound represented by the formula (I-2) include 9-aza-noradamantane-N-oxyl (another name: octahydro-2,5-epimino-pentalen-7-yloxidanyl) (which may hereinafter be abbreviated as "Nor-AZADO"):

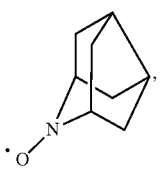

9-aza-noradamantane-N-oxoammonium cation (another name: 7-oxooctahydro-2,5-epiminopentalenium) (which may hereinafter be abbreviated as "Nor-AZADO cation"):

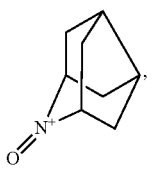

and 9-aza-noradamantan-9-ol (another name: octahydro-2,5-epimino-pentalen-7-ol) (which may hereinafter be abbreviated as "Nor-AZADOH"):

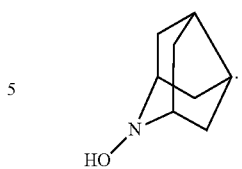

In the present invention, the compound represented by the formula (I-3) include 9-azabicyclo-[3.3.1]nonane-N-oxyl (another name: 9-azabicyclo[3.3.1]non-9-yloxidanyl) (which may hereinafter be abbreviated as "ABNO"):

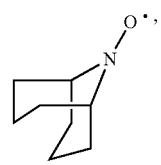

9-azabicyclo-[3.3.1]nonane-N-oxoammonium cation (another name: 9-oxo-9-azoniabicyclo[3.3.1]nonane) (which may hereinafter be abbreviated as "ABNO cation"):

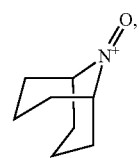

and 9-azabicyclo-[3.3.1]nonan-9-ol (another name: 9-azabicyclo[3.3.1]nonan-9-ol) (which may hereinafter be abbreviated as "ABNOH"):

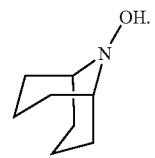

In the present invention, "2,2,6,6-tetramethylpiperidine-N-oxyl" is a compound having a structure represented by the following formula:

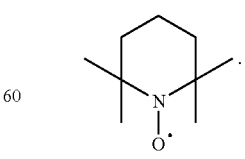

In the present invention, "2,2,6,6-tetramethylpiperidin-1-ol" is a compound having a structure represented by the following formula:

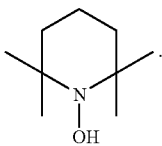

In the present invention, "4-hydroxy-2,2,6,6-tetramethyl-piperidine-N-oxyl" is a compound having a structure represented by the following formula:

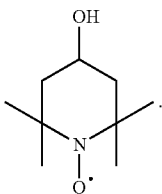

In the present invention, "2,2,6,6-tetramethyl-1,4-piperidinediol" is a compound having a structure represented by the following formula:

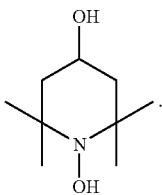

In the present invention, the term "AZADO analogs" means compounds represented by the formula (I-1), (I-2), and (I-3), salts thereof, and solvates thereof.

In the present invention, the term "oxidation catalyst" means an N-oxyl oxidation catalyst and examples include the above-mentioned AZADO analogs and 2,2,6,6-tetramethylpiperidine-N-oxyl, 2,2,6,6-tetramethylpiperidin-1-ol, 4-hydroxy-2,2,6,6-tetramethylpiperidine-N-oxyl, and 2,2,6,6-tetramethyl-1,4-piperidinediol, salts thereof, and solvents thereof. These oxidation catalysts are reagents to be used in an oxidation reaction for synthesizing a ketone compound from an alcohol compound.

In the present invention, the term "weight ratio" means a proportion (ratio) of the weight of a certain substance relative to the weight of a standard substance. For example, the phrase "in the presence of an ammonium ion in a weight ratio of 170 ppm or less relative to Compound (EM)" means that "in the presence of an ammonium ion in an amount of 170 μg or less per 1 g of Compound (EM)".

In the present invention, the term "molar ratio" means a proportion (percentage) of the number of moles of a certain substance relative to the number of moles of a standard substance. For example, the phrase "in the presence of an ammonium ion in a molar ratio of 145% or less relative to the oxidation catalyst" means that "in the presence of an ammonium ion in an amount of 1.45 mol or less per 1 mol of the oxidation catalyst".

In the present invention, the term "unpurified" means that Compound (EM), Compound (E) or Compound (E') obtained by an organic reaction such as addition reaction has not been purified, more specifically, impurities (such as organic matters (for example, an organic compound (by-product) other than the target compound, an organic compound which is a starting material that has remained after the reaction, and an organic reagent), inorganic matters (for example, sodium chloride, ammonium chloride, sodium hydroxide, and potassium hydroxide), and inorganic ions (for example, a cation such as sodium ion, potassium ion, lithium ion, and ammonium ion and an anion such as chloride ion and bromide ion) have not been removed by a conventional purification method, for example, distillation under reduced pressure, high-performance liquid chromatography using silica gel or magnesium silicate, thin-layer chromatography, ion exchange resin, scavenger resin, column chromatography, or recrystallization, or desalting treatment for not only removing organic matters which are impurities but also removing inorganic matters or inorganic ions.

In the present invention, the term "conversion rate" means a percent of an original certain substance (raw material) which has been converted into another substance by a chemical reaction, based on the number of moles of the original certain substance (raw material). For example, the phrase "a preparation process that has provided a conversion rate of 98%" means "a preparation process in which 98% of a substance used as a raw material has been converted into another substance on the basis of the number of moles", in other words, "a preparation process in which 2% of a substance used as a raw material has remained on the basis of the number of moles".

In the present invention, the term "phosphate buffer" means a solution obtained by mixing an aqueous solution of sodium dihydrogen phosphate and an aqueous solution of sodium monohydrogen phosphate at any ratio and the mixed solution has a pH of from about 5.8 to 8.0.

In the present invention, examples of the "oxidizing agent" include sodium hypochlorite (NaOCl), sodium chlorite ($NaClO_2$), sodium bromite ($NaBrO_2$), calcium hypochlorite ($Ca(OCl)_2$), Oxone (trade mark), metachloroperbenzoic acid (MCPBA), iodosylbenzene (PhI=O), iodobenzene diacetate ($PhI(OAc)_2$), orthoperiodic acid ($H_5IO_6$), potassium ferricyanide ($K_3[Fe(CN)_6]$), and N-chlorosuccinic acid imide (NCS).

In the present invention, the "solvent" in "the reaction composition containing a compound selected from the group consisting of 3-[(S)-7-bromo-2-(2-hydroxy-propylamino)-5-pyridin-2-yl-3H-benzo[e][1,4]diazepin-3-yl]propionic acid methyl ester, 3-[(S)-7-bromo-2-((R)-2-((R)-2-hydroxy-proxy-propylamino)-5-pyridin-2-yl-3H-benzo[e][1,4]diazepin-3-yl]propionic acid methyl ester, and 3-[(S)-7-bromo-2-((S)-2-hydroxy-propylamino)-5-pyridin-2-yl-3H-benzo[e][1,4]diazepin-3-yl]propionic acid methyl ester, an oxidizing agent, an oxidation catalyst, and a solvent", that is, the "solvent" to be used in the oxidation reaction is an organic solvent (for example, ethyl acetate, methyl acetate, toluene, methylene chloride, dichloroethane, acetonitrile, dimethylsulfoxide, or acetone, or a solvent obtained by mixing these organic solvents as needed) or a mixed solvent of the above-mentioned organic solvent and water.

In the present invention, the term "reaction composition" means an assembly of organic matters and inorganic matters present in the reaction system of a chemical reaction. For example, in an oxidation reaction, the reaction composition of the oxidation reaction contains a starting material, a reaction reagent (such as oxidizing agent), a reaction catalyst (such as oxidation catalyst), and a solvent and it may further contain an inorganic salt (such as ammonium chloride, ammonium bromide, ammonium acetate, ammonium carbonate, sodium monohydrogen phosphate, and sodium dihydrogen phosphate), and an inorganic ion (such as ammonium ion, chloride ion, bromide ion, acetate ion, carbonate ion, phosphate ion, and sodium ion).

In the present invention, $R_1$ is preferably hydrogen, fluorine, or methyl, more preferably hydrogen or methyl, particularly preferably hydrogen.

In the present invention, $R_2$ is preferably hydrogen, fluorine, a hydroxyl group, or methoxy, more preferably hydrogen.

In the present invention, $R_3$ is preferably hydrogen or fluorine, more preferably hydrogen.

In the present invention, $R_5$ is preferably hydrogen or methyl, more preferably hydrogen.

In the present invention, X is preferably nitrogen (N) or an ammonium cation ($N^+$), more preferably nitrogen.

In the present invention, $R_4$ is preferably an oxygen radical (O.), a hydroxyl group (OH), or oxygen (O), more preferably an oxygen radical or a hydroxyl group, particularly preferably a hydroxyl group.

In the present invention,

 is a single bond or a double bond, preferably a single bond.

In the present invention,

XR$_4$ is preferably
N—O. or N—OH,
more preferably
N—OH.

In the intention, the compound represented by the formula (I-1) is preferably AZADO, AZADO cation, AZADOH, Me-AZADO, Me-AZADO cation, Me-AZADOH, 5-OH-1-Me-AZADO, 5-OH-1-Me-AZADO cation, 5-OH-1-Me-AZADOH, 5-MeO-1-Me-AZADO, 5-MeO-1-Me-AZADO cation, 5-MeO-1-Me-AZADOH, 5-F-1-Me-AZADO, 5-F-1-Me-AZADO cation, 5-F-1-Me-AZADOH, 1-F-AZADO, 1-F-AZADO cation, 1-F-AZADOH, 5-F-AZADO, 5-F-AZADO cation, 5-F-AZADOH, 5,7-diF-1-Me-AZADO, 5,7-diF-1-Me-AZADO cation, 5,7-diF-1-Me-AZADOH, 1,3-diMe-AZADO, 1,3-diMe-AZADO cation, or 1,3-diMe-AZADOH, more preferably AZADO, AZADO cation, AZADOH, Me-AZADO, Me-AZADO cation, or Me-AZADOH, still more preferably AZADO, AZADO cation, or AZADOH, still more preferably AZADO or AZADOH, particularly preferably AZADOH.

In the present invention, the compound represented by the formula (I-2) is preferably Nor-AZADO, Nor-AZADO cation, or Nor-AZADOH, more preferably Nor-AZADO.

In the present invention, the compound represented by the formula (I-3) is preferably ABNO, ABNO cation, or ABNOH, more preferably ABNO.

In the present invention, the oxidation catalyst is preferably AZADO, AZADO cation, AZADOH, Me-AZADO, Me-AZADO cation, Me-AZADOH, 5-OH-1-Me-AZADO, 5-OH-1-Me-AZADO cation, 5-OH-1-Me-AZADOH, 5-MeO-1-Me-AZADO, 5-MeO-1-Me-AZADO cation, 5-MeO-1-Me-AZADOH, 5-F-1-Me-AZADO, 5-F-1-Me-AZADO cation, 5-F-1-Me-AZADOH, 1-F-AZADO, 1-F-AZADO cation, 1-F-AZADOH, 5-F-AZADO, 5-F-AZADO cation, 5-F-AZADOH, 5,7-diF-1-Me-AZADO, 5,7-diF-1-Me-AZADO cation, 5,7-diF-1-Me-AZADOH, 1,3-diMe-AZADO, 1,3-diMe-AZADO cation, 1,3-diMe-AZADOH, Nor-AZADO, Nor-AZADO cation, Nor-AZADOH, ABNO, ABNO cation, or ABNOH, more preferably AZADO, AZADO cation, AZADOH, Me-AZADO, Me-AZADO cation, Me-AZADOH, Nor-AZADO, or ABNO, still more preferably AZADO, AZADO cation, or AZADOH, still more preferably AZADO or AZADOH, particularly preferably AZADOH.

In the present invention, the conversion rate is preferably 98% or more, more preferably 98.5% or more, still more preferably 99% or more, still more preferably 99.5% or more, particularly preferably 100%.

In the present invention, in order to attain the conversion rate falling within the above-mentioned preferred range, it is recommended, in the reaction system of the oxidation reaction, to adjust the weight ratio of an ammonium ion, relative to each of Compound (EM), Compound (E), and Compound (E'), to a predetermined level or less; to adjust the molar ratio of an ammonium ion relative to the oxidation catalyst to a predetermined level or less; or to satisfy both.

The weight ratio of an ammonium ion relative to each of Compound (EM), Compound (E), and Compound (E') is at least about 170 ppm or less, preferably about 111 ppm or less, more preferably about 91 ppm or less, still more preferably about 72 ppm or less, still more preferably about 53 ppm or less, particularly preferably about 33 ppm or less.

The molar ratio of an ammonium ion relative to the oxidation catalyst is at least about 145% or less, preferably about 94% or less, more preferably about 78% or less, still more preferably about 61% or less, still more preferably about 45% or less, particularly preferably about 28% or less.

Compound (FK) can be obtained from each of Compound (EM), Compound (E), and Compound (E') at the above-mentioned preferable conversion rate by adjusting the weight ratio of an ammonium ion relative to each of Compound (EM), Compound (E), and Compound (E') to fall within the above-mentioned range, by adjusting the molar ratio of an ammonium ion relative to the oxidation catalyst to fall within the above-mentioned range, or by satisfying both.

In the present invention, Compound (EM) to be used in the oxidation reaction is preferably obtained by conducting an addition reaction between Compound (D) and 1-aminopropan-2-ol and then washing.

In the present invention, Compound (E) to be used in the oxidation reaction is preferably obtained by conducting an addition reaction between Compound (D) and (R)-1-aminopropan-2-ol and then washing.

In the present invention, Compound (E') to be used in the oxidation reaction is preferably obtained by conducting an addition reaction between Compound (D) and (S)-1-aminopropan-2-ol or and then washing.

In the present invention, the term "washing" in the phrase "obtained by conducting an addition reaction between Compound (D) and 1-aminopropan-2-ol, (R)-1-aminopropan-2-ol, or (S)-1-aminopropan-2-ol and then washing" means a work-up operation, which is to be conducted after the addition reaction, with a solution having a pH near a weakly acidic to weakly basic range (from about pH 3.5 to about pH 10.5, preferably from about pH 4.5 to about pH 9.0), particularly preferably a pH near a weakly acidic to neutral range (from about pH 5.5 to about pH 8.0) and having a buffer action. The solution used for washing is a water soluble solution and examples include an aqueous solution of ammonium chloride (from about pH 4.5 to pH 6.0), an aqueous solution of sodium monohydrogen phosphate (about pH 9.5), an aqueous solution of sodium dihydrogen phosphate (from about pH 3.8 to about pH 4.5), a phosphate buffer (from about pH 5.8 to about pH 8.0), a potassium phosphate buffer (about pH 10.0), a phosphate buffer saline (about pH 7.4), an acetate buffer (acetic acid+sodium acetate; from about pH 3.6 to pH 5.6), a citrate buffer (citric acid+sodium citrate; from about pH 3.0 to about pH 6.2), a citrate-phosphate buffer (from about pH 2.6 to about pH 7.0), a borate buffer (from about pH 8.0 to about pH 10.3), and a tartrate buffer (from about pH 2.9 to about pH 4.2).

In the present invention, a washing method is preferably a method of washing with an aqueous solution of ammonium chloride, an aqueous solution of sodium dihydrogen phosphate, an aqueous solution of sodium monohydrogen phosphate, or a phosphate buffer (a mixed solution obtained by mixing an aqueous solution of sodium dihydrogen phosphate and an aqueous solution of sodium monohydrogen phosphate at any ratio); more preferably a method of washing with an aqueous solution of sodium dihydrogen phosphate, an aqueous solution of sodium monohydrogen phosphate, or a phosphate buffer; still more preferably, a method of washing with an aqueous solution of sodium dihydrogen phosphate or a phosphate buffer; particularly preferably a method of washing with a phosphate buffer.

In the present invention, as is apparent for those skilled in the art, the symbol:

⋯⋯ represents bonding to the opposite side of the paper plane (that is, α-configuration); the symbol:

◢ represents bonding to the near side of the paper plane (that is, β-configuration); the symbol:

∿ represents α-configuration or β-configuration; and the symbol:

╱ represents a mixture of the α-configuration and the β-configuration at any ratio, unless otherwise noted.

Salt:

The compound represented by the formula (I-1), (I-2), or (I-3), 2,2,6,6-tetramethylpiperidine-N-oxyl, 2,2,6,6-tetramethylpiperidin-1-ol, 4-hydroxy-2,2,6,6-tetramethylpiperidine-N-oxyl, or 2,2,6,6-tetramethyl-1,4-piperidinediol is converted into a salt thereof by a known method.

The salt is preferably a pharmaceutically acceptable salt.
The salt is preferably water soluble.
Examples of the salt include acid addition salts.
Examples of the acid addition salts include inorganic acid salts such as hydrochloride, hydrobromide, hydroiodide, sulfate, phosphate, nitrate, borate, tetrafluoroborate, perchlorate, antimonate, and hexafluorophosphate and organic acid salts such as acetate, lactate, tartrate, benzoate, citrate, methanesulfonate, ethanesulfonate, trifluoroacetate, benzenesulfonate, toluenesulfonate, isethionate, glucuronate, and gluconate.

In the present invention, the acid addition salt is preferably an inorganic acid salt or an acetate, more preferably, a hydrochloride, a hydrobromide, a hydroiodide, a sulfate, a phosphate, a nitrate, a borate, a tetrafluoroborate, a perchlorate, an antimonate, a hexafluorophosphate, or an acetate, particularly preferably a hydrochloride, a nitrate, a tetrafluoroborate, or an acetate.

Solvate:

The compound represented by the formula (I-1), (I-2), or (I-3), 2,2,6,6-tetramethylpiperidine-N-oxyl, 2,2,6,6-tetramethylpiperidin-1-ol, 4-hydroxy-2,2,6,6-tetramethylpiperidine-N-oxyl, or 2,2,6,6-tetramethyl-1,4-piperidinediol, or a salt thereof is converted into a solvate thereof by a known method. The solvate is preferably nontoxic and water soluble. Examples of the suitable solvate include solvates with water or an alcoholic solvent (for example, ethanol).

Atoms each constituting Compound (D), Compound (EM), Compound (E), Compound (E'), Compound (FK), Compound (P), the formula (I-1), the formula (I-2), and the formula (I-3) may be substituted by an isotope thereof (for example, $^2H$, $^3H$, $^{13}C$, $^{14}C$, $^{15}N$, $^{16}N$, $^{17}O$, or $^{18}O$).

The preparation process according to the present invention will next be described. First, a process for preparing Compound (FK) from Compound (EM) according to the present invention is shown by the following reaction scheme 1.

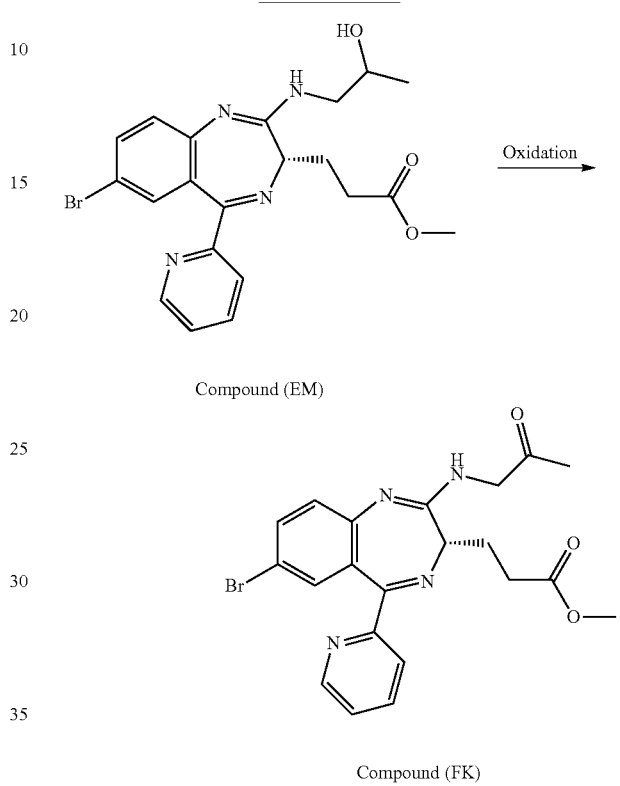

Reaction scheme 1

Compound (EM)

Compound (FK)

Compound (EM) can be prepared readily by a known method, for example, a method shown below in the reaction scheme 2, a method based thereon, the method described in "Comprehensive Organic Transformations: A Guide to Functional Group Preparations 2nd Edition (Richard C. Larock, John Wiley & Sons Inc, 1999)", or the method described in WO 2000/069836.

Incidentally, Compound (EM) may be used as a salt thereof.

As such a salt, a pharmaceutically acceptable salt, for example, an acid addition salt may be used.

As the acid addition salt, for example, those described as an acid addition salt in the above column [salt] may be used.

Compound (EM) or salt thereof used in the reaction scheme 1 may be used as a solvate thereof.

Examples of the solvate include solvates with water or with an alcoholic solvent (for example, ethanol).

In the oxidation reaction for preparing Compound (FK) from Compound (EM) described in the reaction scheme 1, using an unpurified Compound (EM) is novel. In addition, using an AZADO analog as an oxidation catalyst to be used in the oxidation reaction for preparing Compound (FK) from Compound (EM) is novel. Compound (FK) available by this reaction can be prepared, for example, by reacting Compound (EM) which may be unpurified at a temperature of from about −20° C. to 50° C. in an organic solvent (for example, ethyl acetate, methyl acetate, toluene, methylene chloride, dichloroethane, acetonitrile, dimethylsulfoxide, or acetone, or a solvent obtained by mixing the above-mentioned organic solvents as needed) or a mixed solvent of such an organic solvent and water, in the presence or absence of a base (for example, sodium hydrogen carbonate, sodium carbonate, 1,4-diazabicyclo[2.2.2]octane, or potassium hydroxide, or a base obtained by mixing the above-mentioned bases as needed) or an aqueous solution of such a base, in the presence or absence of an inorganic salt (for example, sodium bromide, potassium bromide, potassium chloride, copper chloride, copper bromide, butylammonium bromide, butylammonium chloride, sodium nitrite, or sodium acetate, or an inorganic salt obtained by mixing these inorganic salts as needed), and in the presence of an oxidizing agent (for example, sodium hypochlorite (NaOCl), sodium chlorite (NaClO$_2$), sodium hypobromite (NaBrO$_2$), calcium hypochlorite (Ca(OCl)$_2$), Oxone (trade mark), metachloroperbenzoic acid (MCPBA), iodosylbenzene (PhI=O), iodobenzene diacetate (PhI(OAc)$_2$), ortho-periodic acid (H$_5$IO$_6$), potassium ferricyanide (K$_3$[Fe(CN)$_6$]), or N-chlorosuccinic acid imide (NCS), or an oxidizing agent obtained by mixing the above-mentioned oxidizing agents as needed) and the above-mentioned oxidation catalyst (for example, AZADO analogs (for example, AZADO, Me-AZADO, AZADOH, Nor-AZADO, or ABNO, or an oxidation catalyst obtained by mixing the above-mentioned oxidation catalysts as needed)).

As another process, Compound (FK) can be prepared, for example, by subjecting Compound (EM) which may be unpurified to an air (oxygen) oxidation reaction at a temperature of from about 0° C. to 80° C. in an organic solvent (for example, ethyl acetate, toluene, methylene chloride, dichloroethane, acetonitrile, dimethylsulfoxide, acetone, or acetic acid, or a solvent obtained by mixing the above-mentioned organic solvents as needed) or a mixed solvent of such an organic solvent and water, in the presence or absence of a base (for example, sodium hydrogen carbonate, sodium carbonate, 1,4-diazabicyclo[2.2.2]octane, or potassium hydroxide, or a base obtained by mixing these bases as needed) or an aqueous solution of such a base, in the presence or absence of an inorganic salt (for example, sodium bromide, potassium bromide, potassium chloride, copper chloride, copper bromide, butylammonium bromide, or butylammonium chloride, or an inorganic salt obtained by mixing the above-mentioned inorganic salts as needed), in the presence of the above-mentioned oxidation catalyst (for example, AZADO analogs (for example, AZADO, Me-AZADO, AZADOH, Nor-AZADO, or ABNO, or an oxidation catalyst obtained by mixing the above-mentioned oxidation catalysts as needed).

As a further process, Compound (FK) can be prepared by subjecting, instead of Compound (EM), Compound (E) or Compound (E') to the above-mentioned oxidation reaction.

The compound subjected to the oxidation reaction in the present invention is preferably Compound (E) or Compound (E'), more preferably Compound (E).

Compound (EM) can be prepared, for example, by the process shown in the following reaction scheme 2.

Reaction scheme 2

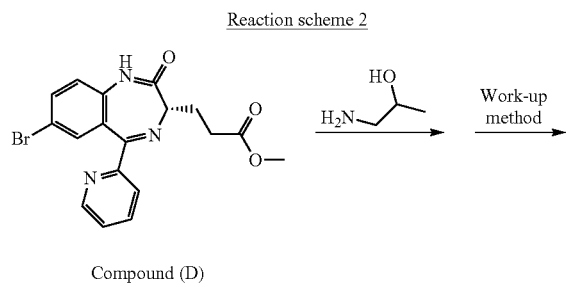

Compound (D)

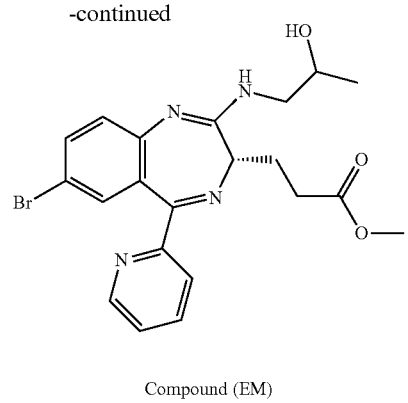

Compound (EM)

The reaction for preparing Compound (EM) from Compound (D) in the reaction scheme 2 is a known one. A work-up method in the reaction scheme 2 for preparing Compound (FK) at a markedly high conversion rate (reaction efficiency) is however utterly unknown when Compound (EM) obtained by the above reaction, particularly when it is an unpurified compound, is subjected to the oxidation reaction (in the above reaction scheme 1) in the next step.

Compound (EM) can be prepared, for example, by using Compound (D), adding thereto 1-aminopropan-2-ol, and reacting the resulting mixture at a temperature of from about −80° C. to 50° C. in an organic solvent (for example, tetrahydrofuran (THF), diethyl ether, tert-butyl methyl ether (t-BuOMe), dioxane, hexamethylphosphoric acid triamide (HMPA), acetonitrile, toluene, ethylbenzene, diglyme, heptane, hexane, or cyclohexane, or a solvent obtained by mixing the above-mentioned organic solvents as needed), in the presence of a base (for example, lithium diisopropylamide (LDA), lithium bis(trimethylsilyl)amide (LiN(TMS)$_2$), sodium bis(trimethylsilyl)amide (NaN(TMS)$_2$), potassium bis(trimethylsilyl)amide (KN(TMS)$_2$), n-butyl lithium, sec-butyl lithium, or tert-butyl lithium, or a base obtained by mixing the above-mentioned bases as needed), in the presence or absence of an inorganic salt (for example, lithium chloride, lithium bromide, zinc chloride, or palladium diacetate (Pd(OAc)$_2$), or an inorganic salt obtained by mixing the above-mentioned inorganic salts as needed), in the presence of an activating reagent (for example, trifluoromethanesulfonic anhydride ((CF$_3$SO$_2$)$_2$O), diethyl chlorophosphate ((EtO)$_2$P(O)Cl), trichlorosilane (TMSCl), phosphoryl chloride (P(O)Cl$_3$), or bismorpholinophosphoryl chloridate (BMPC):

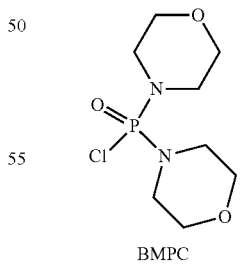

BMPC or a reagent obtained by mixing the above-mentioned activating reagents as needed).

The work-up method to be conducted after the reaction for preparing Compound (EM) from Compound (D) in the reaction scheme 2 can be positioned as one of the characteristics of the present invention. The work-up method is preferably conducted in a water soluble solution near a pH range from weakly acidic to weakly alkaline (from about pH 3.5 to about pH 10.5). The water soluble solution is more preferably near a pH range to from weakly acidic to weakly alkaline (from about pH 4.5 to about 9.0), particularly preferably near a pH range from weakly acidic to neutral (from about pH 5.5 to about 8.0). Such a work-up method can be classified roughly into two methods: that is, a method including a step of quenching with an ammonium ion-containing solution and a method including a step of quenching with an ammonium ion-free solution.

The method including a step of quenching with an ammonium ion-containing solution can be conducted by adding an aqueous solution of ammonium chloride in a reaction vessel in which the reaction for preparing Compound (EM) from Compound (D) has been conducted by the above-mentioned process to quench and then conducting sufficient water washing of the organic layer obtained by a separation operation. It can also be conducted by adding, to an aqueous solution of ammonium chloride, the reaction mixture obtained by the reaction for preparing Compound (EM) from Compound (D), to quench and then subjecting the resulting mixture to sufficient water washing.

The term "sufficient water washing" as used herein means continuing water washing until the remaining content of an ammonium ion in the organic layer decreases to at least about 170 ppm or less, preferably about 111 ppm or less, more preferably about 91 ppm or less, still more preferably about 72 ppm or less, still more preferably about 53 ppm or less, particularly preferably about 33 ppm or less, relative to Compound (EM); continuing water washing until the molar ratio of an ammonium ion in the organic layer decreases to at least about 145% or less, preferably about 94% or less, more preferably about 78% or less, more preferably about 61% or less, still more preferably 45% or less, particularly preferably about 28% or less, relative to an oxidation catalyst used for the oxidation reaction of Compound (EM); or continuing water washing until both of the above-mentioned conditions are satisfied.

The method including a step of quenching with an ammonium ion-free solution can be conducted by adding, to a reaction vessel in which the reaction for preparing Compound (EM) from Compound (D) has been conducted, an aqueous solution of sodium dihydrogen phosphate, an aqueous solution of sodium monohydrogen phosphate, a phosphate buffer, a potassium phosphate buffer, a phosphate buffer saline, an acetate buffer (acetic acid+sodium acetate), a citrate buffer (citric acid+sodium citrate), a citrate-phosphate buffer, a borate buffer, or a tartrate buffer to quench and then conducting water washing of the organic layer obtained by a separation operation. It can also be conducted by adding the reaction mixture obtained by the reaction for preparing Compound (EM) from Compound (D) to an aqueous solution of sodium dihydrogen phosphate, an aqueous solution of sodium monohydrogen phosphate, a phosphate buffer, a potassium phosphate buffer, a phosphate buffer saline, an acetate buffer (acetic acid+sodium acetate), a citrate buffer (citric acid+sodium citrate), a citrate-phosphate buffer, a borate buffer, or a tartrate buffer to quench and then conducting water washing of the organic layer as described above. Different from the water washing conducted when the above-mentioned aqueous solution of ammonium chloride is used, no particular limitation is imposed on the water washing in this operation and water washing at only once is sufficient. The solution to be used in such a step of quenching with an ammonium ion-free solution is preferably an aqueous solution of sodium dihydrogen phosphate, an aqueous solution of sodium monohydrogen phosphate, and/or a phosphate buffer, more preferably an aqueous solution of sodium dihydrogen phosphate and/or a phosphate buffer, particularly preferably a phosphate buffer.

By conducting the work-up so as to create, in the reaction system of a subsequent oxidation reaction, a circumstance containing an ammonium ion as less as possible, the oxidation reaction from Compound (EM) to Compound (FK) can be conducted at a markedly high conversion rate (reaction efficiency) with good reproducibility.

In the present invention, from the unpurified compound (EM) obtained by the above-mentioned work-up method, Compound (FK) can be prepared even without conducting purification such as distillation, silica gel chromatography, or recrystallization as described above, because the oxidation reaction proceeds at a markedly high conversion rate (reaction efficiency) with good reproducibility.

In the present invention, Compound (E) obtained by using (R)-1-aminopropan-2-ol or Compound (E') obtained by using (S)-1-aminopropan-2-ol can be obtained in a manner similar to that of the above-mentioned reaction scheme 2, instead of Compound (EM) obtained by using 1-aminopropan-2-ol in the reaction scheme 2.

Compound (FK) in the present invention is an important synthesis intermediate of Compound (P) having sedative and anesthetic actions. Compound (P) is useful as a sedative or an anesthetic.

This application claims priority to Japanese Patent Application No. 2013-041492 filed on Mar. 4, 2013, the entire contents of which are incorporated by reference herein.

In this specification, all the contents of the patent documents, non-patent documents, and reference documents explicitly cited herein can be cited as a part of the specification.

EXAMPLES

The present invention will hereinafter be described by Examples, but it is not limited to or by them.

The solvent in parentheses shown in the description of separation by chromatography or TLC is an eluting solvent or developing solvent used therefor and a ratio means a ratio by volume.

The solvent in parentheses shown in the description of NMR is a solvent used in measurement.

The compound name used herein is named using ACD/Name (trade mark) which is a computer program for naming generally based on the IUPAC rules or named according to IUPAC nomenclature.

Example 1

Reaction from 3-[(S)-7-bromo-2-oxo-5-pyridin-2-yl-2,3-dihydro-1H-1,4-benzodiazepin-3-yl]propionic acid methyl ester (Compound (D)) to 3-[(S)-7-bromo-2-(2-hydroxy-propylamino)-5-pyridin-2-yl-3H-benzo[e][1,4]diazepin-3-yl]propionic acid methyl ester (Compound (EM))

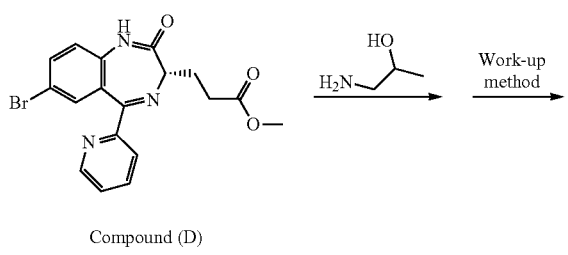

Compound (D)

-continued

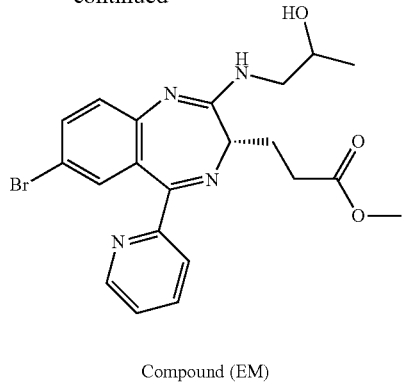

Compound (EM)

To Compound (D) (1.0 mmol) in 1.0 mL of tetrahydrofuran was added bismorpholinophosphoryl chloridate (BMPC) (1.2 mmol). At 0° C. or less, a tetrahydrofuran solution (1.8 M, 1.0 mmol, 0.56 mL) of lithium diisopropylamide was added dropwise to the reaction mixture. At 0° C., a solution of 1-aminopropan-2-ol (1.3 mmol) in 0.4 mL of tetrahydrofuran was added dropwise to the reaction mixture. The resulting reaction mixture was stirred overnight at 0° C.

Example 2

Work-Up Method in Synthesis of Compound (EM)

Example 2-1

Work-Up Method with Aqueous Solution of Ammonium Chloride

To the reaction mixture of Example 1 were added about 16 mL of t-butyl methyl ether and about 10 mL of an aqueous solution of ammonium chloride (concentration: 25%) to separate it into layers. The organic layer thus obtained was washed with about 10 mL of an aqueous solution of ammonium chloride and then washed with water so as to decrease the weight ratio of an ammonium ion content in the organic layer to 170 ppm or less relative to Compound (EM). The organic layer thus obtained was concentrated to about 1.0 mL under reduced pressure. Toluene was added to the organic layer, followed by concentration under reduced pressure to about 1.0 mL. The toluene solution thus obtained was cooled to 0° C. The solid thus precipitated was collected by filtration and then dried to obtain Compound (EM) having the following physical properties. The measurement procedure of an ammonium ion content will be described later.

TLC: Rf 0.35 (ethyl acetate);
$^1$H-NMR (CDCl$_3$): δ 8.70-8.60 (m, 1H), 7.88-7.82 (m, 1H), 7.81-7.75 (m, 1H), 7.53-7.47 (m, 1H), 7.40-7.33 (m, 2H), 7.15-7.10 (m, 1H), 5.71-5.65 (m, 1H), 5.20-4.70 (m, 1H), 4.15-3.95 (m, 1H), 3.71 (s, 3H), 3.48-3.38 (m, 1H), 3.33-3.14 (m, 1H), 3.30-3.20 (m, 1H), 2.85-2.73 (m, 1H), 2.66-2.35 (m, 3H), 1.20-1.18 (m, 3H).
HPLC Conditions
Column: YMC-Pack ODS-AQ (length: 25 cm, inner diameter: 4.6 mm, particle size: 3 μm, YMC)
Column temperature: 25° C.
Mobile phase: 10 mM aqueous potassium dihydrogen phosphate solution/acetonitrile=55/45
Flow rate: 0.7 mL/min
Detector: UV 230 nm
Injection amount: 5 μL
Analysis time: 40 minutes
The retention time under the above-mentioned conditions is 12.3 minutes and 12.8 minutes.

Example 2-2

Work-Up Method with Sodium Dihydrogen Phosphate and/or Phosphate Buffer

To the reaction mixture of Example 1 were added about 16 mL of t-butyl methyl ether and about 16 mL of an aqueous solution of sodium dihydrogen phosphate (concentration: 20%) to separate it into layers. The organic layer thus obtained was washed with about 10 mL of a phosphate buffer and then washed twice with water (about 5 mL). The organic layer thus obtained was concentrated to about 1.0 mL under reduced pressure. Toluene was added to the organic layer and the resulting mixture was concentrated to about 1.0 mL under reduced pressure. The toluene solution thus obtained was cooled to 0° C. The solid thus precipitated was collected by filtration and then dried to obtain Compound (EM) having the following physical properties.

TLC: Rf 0.35 (ethyl acetate)
$^1$H-NMR (CDCl$_3$): δ 8.70-8.60 (m, 1H), 7.88-7.82 (m, 1H), 7.81-7.75 (m, 1H), 7.53-7.47 (m, 1H), 7.40-7.33 (m, 2H), 7.15-7.10 (m, 1H), 5.71-5.65 (m, 1H), 5.20-4.70 (m, 1H), 4.15-3.95 (m, 1H), 3.71 (s, 3H), 3.48-3.38 (m, 1H), 3.33-3.14 (m, 1H), 3.30-3.20 (m, 1H), 2.85-2.73 (m, 1H), 2.66-2.35 (m, 3H), 1.20-1.18 (m, 3H).
HPLC Conditions
Column: YMC-Pack ODS-AQ (length: 25 cm, inner diameter: 4.6 mm, particle size: 3 μm, YMC)
Column temperature: 25° C.
Mobile phase: 10 mM aqueous potassium dihydrogen phosphate solution/acetonitrile=55/45
Flow rate: 0.7 mL/min
Detector: UV 230 nm
Injection amount: 5 μL
Analysis time: 40 minutes
The retention time under the above-mentioned conditions is 12.3 minutes and 12.8 minutes.

Example 3

Preparation of 3-[(S)-7-bromo-2-(2-oxo-propylamino)-5-pyridin-2-yl-3H-1,4-benzodiazepin-3-yl] propionic acid methyl ester (Compound (FK)) from 3-[(S)-7-bromo-2-(2-hydroxy-propylamino)-5-pyridin-2-yl-3H-benzo[e][1,4]diazepin-3-yl]propionic acid methyl ester (Compound (EM))

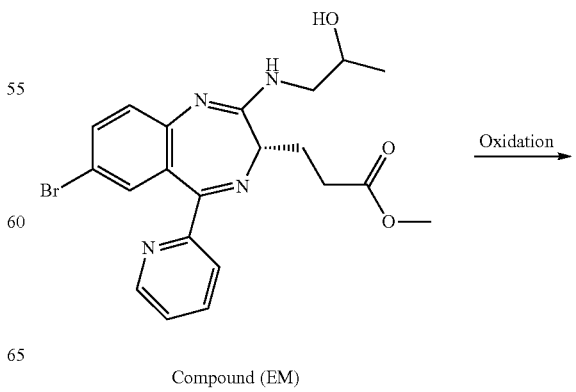

Compound (EM)

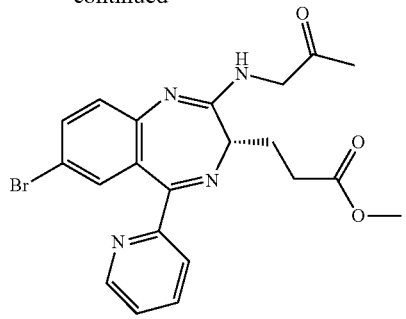

Compound (FK)

Example 3-1

Oxidation Reaction Using AZADO as Oxidation Catalyst

To the unpurified compound (EM) (1.0 mmol) obtained in Example 1 and Example 2 in a mixed solvent of 3.4 mL of methyl acetate and 5.7 mL of toluene were added 0.46 mg of AZADO (0.003 mol), 1.9 mL of an aqueous solution of sodium hydrogen carbonate (7.7 wt %), and 6.0 mg of potassium bromide (0.05 mmol). At 0° C., 640 mg of an aqueous solution of sodium hypochlorite (14 wt %; 1.2 mmol) was added to the reaction mixture. The resulting mixture was stirred at 0° C. for one hour, followed by HPLC to find a conversion rate and confirm disappearance of the raw material. To the reaction mixture was added an aqueous solution of sodium thiosulfate to separate it into layers. The organic layer thus obtained was washed with an aqueous solution of ammonium chloride. The resulting organic layer was concentrated under reduced pressure. To the residue thus obtained were added toluene and methanol, followed by azeotropy to obtain Compound (FK) having the following physical properties.

TLC: Rf 0.45 (ethyl acetate);
HPLC Conditions
Column: YMC-Pack ODS-AQ (length: 25 cm, inner diameter: 4.6 mm, particle size: 3 μm, YMC)
Column temperature: 25° C.
Mobile phase: 10 mM aqueous potassium dihydrogen phosphate solution/acetonitrile=55/45
Flow rate: 0.7 mL/min
Detector: UV 230 nm
Injection amount: 5 μL
Analysis time: 40 minutes
The retention time under the above-mentioned conditions is 16.9 minutes.

Example 3-2

Oxidation Reaction Using AZADOH as Oxidation Catalyst

By an operation similar to that of Example 3-1 except for the use of 0.46 mg of AZADOH (0.003 mmol) instead of AZADO, Compound (FK) having the following physical properties was obtained.

TLC: Rf 0.45 (ethyl acetate);
HPLC conditions
Column: YMC-Pack ODS-AQ (length: 25 cm, inner diameter: 4.6 mm, particle size: 3 μm, YMC)
Column temperature: 25° C.
Mobile phase: 10 mM aqueous potassium dihydrogen phosphate solution/acetonitrile=55/45
Flow rate: 0.7 mL/min
Detector: UV 230 nm
Injection amount: 5 μL
Analysis time: 40 minutes
The retention time under the above-mentioned conditions is 16.9 minutes.

Example 4

Synthesis of 3-[(S)-7-bromo-2-((R)-2-hydroxy-propylamino)-5-pyridin-2-yl-3H-benzo[e][1,4]diazepin-3-yl]propionic acid methyl ester ("Compound (E)")

By operations similar to those of Example 1 and Example 2 except for the use of (R)-1-aminopropan-2-ol instead of 1-aminopropan-2-ol, Compound (E) having the following physical properties was obtained.

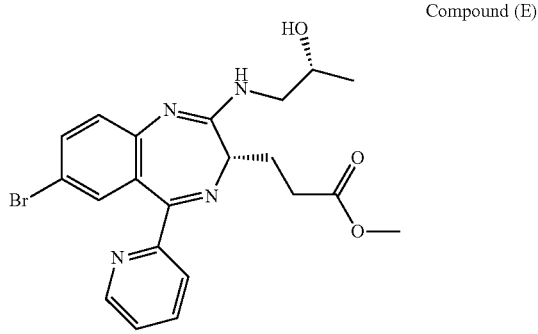 [SMILES: COC(=O)CC[C@@H]1N=C(c2ccccn2)c2cc(Br)ccc2N=C1NC[C@@H](C)O]

Compound (E)

TLC: Rf 0.35 (ethyl acetate);
$^1$H-NMR (CDCl$_3$): δ 8.66 (ddd, J=4.9, 1.7, 0.9 Hz, 1H), 7.85 (d, J=7.6 Hz, 1H), 7.78 (td, J=7.6, 1.6 Hz, 1H), 7.50 (dd, J=8.8, 2.4 Hz, 1H), 7.38 (d, J=2.4 Hz, 1H), 7.40-7.33 (m, 1H), 7.12 (d, J=8.8 Hz, 1H), 5.69 (t, J=5.4 Hz, 1H), 5.17 (s, 1H), 4.06-3.93 (m, 1H), 3.71 (s, 3H), 3.48-3.38 (m, 1H), 3.33 (dd, J=10.0, 4.0 Hz, 1H), 3.26 (ddd, J=14.2, 6.4, 2.0 Hz, 1H), 2.85-2.73 (m, 1H), 2.66-2.35 (m, 3H), 1.17 (d, J=6.4 Hz, 3H).

HPLC Conditions
Column: YMC-Pack ODS-AQ (length: 25 cm, inner diameter: 4.6 mm, particle size: 3 μm, YMC)
Column temperature: 25° C.
Mobile phase: 10 mM aqueous potassium dihydrogen phosphate solution/acetonitrile=55/45
Flow rate: 0.7 mL/min
Detector: UV 230 nm
Injection amount: 5 μL
Analysis time: 40 minutes
The retention time under the above-mentioned conditions is 12.8 minutes.

Example 5

Preparation of Compound (FK) from Compound (E)

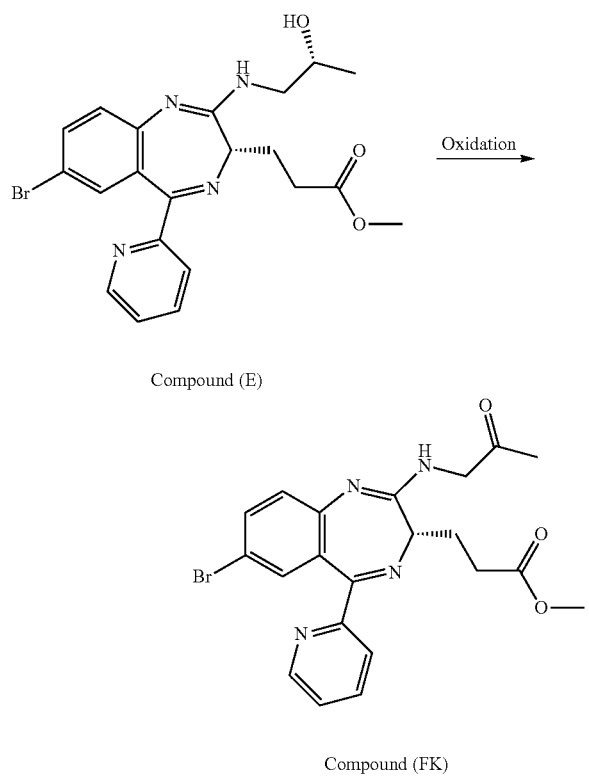

Compound (E)

Oxidation →

Compound (FK)

An operation similar to that of Example 3 (Example 3-1 or Example 3-2) was conducted using Compound (E) prepared in Example 4 to obtain Compound (FK) having the following physical properties.

TLC: Rf 0.45 (ethyl acetate);
HPLC Conditions
Column: YMC-Pack ODS-AQ (length: 25 cm, inner diameter: 4.6 mm, particle size: 3 μm, YMC)
Column temperature: 25° C.
Mobile phase: 10 mM aqueous potassium dihydrogen phosphate solution/acetonitrile=55/45
Flow rate: 0.7 mL/min
Detector: UV 230 nm
Injection amount: 5 μL
Analysis time: 40 minutes
The retention time under the above-mentioned conditions is 16.9 minutes.

Example 6

Preparation of Compound (P) from Compound (FK)

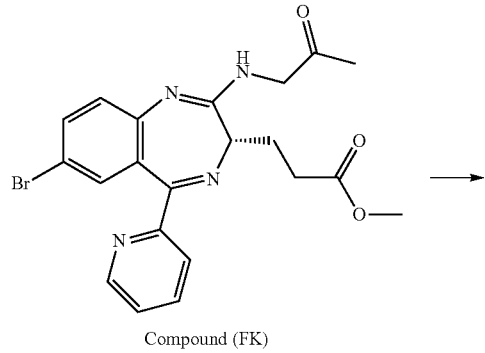

Compound (FK) →

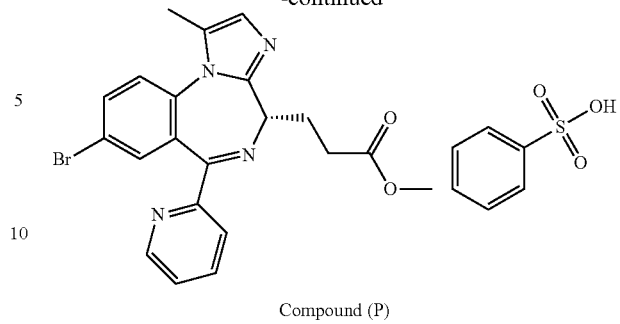

Compound (P)

To Compound (FK) prepared in Example 3 were added 32 mg of benzenesulfonic acid and 0.46 mL of methanol. The resulting mixture was stirred at 50° C. for five hours. After filtering the reaction mixture, 110 mg of benzenesulfonic acid and 0.2 mL of methanol were added to obtain Compound (P)

TLC: Rf 0.42 (n-hexane/ethyl acetate=20/80)
$^1$H-NMR (CDCl$_3$): δ 16.0 (br s, 1H), 8.59 (d, J=4.2 Hz, 1H), 8.18 (d, J=8.4 Hz, 1H), 7.95-7.90 (m, 2H), 7.88-7.84 (m, 1H), 7.84 (dd, J=8.6, 2.2 Hz, 1H), 7.75 (d, J=2.2 Hz, 1H), 7.51-7.48 (m, 1H), 7.50 (d, J=8.6 Hz, 1H), 7.45-7.41 (m, 1H), 7.39-7.35 (m, 3H), 4.41 (dd, J=9.9, 3.9 Hz, 1H), 3.61 (s, 3H), 2.98-2.89 (m, 1H), 2.83-2.68 (m, 3H), 2.42 (s, 3H).

HPLC Conditions
Column: Cadenza CD-18 (length: 15 cm, inner diameter: 4.6 mm, particle size: 3 μm, Imtakt)
Column temperature: 40° C.
Mobile phase: A: 10 mM aqueous potassium dihydrogen phosphate solution, B: methanol
A/B=from 50/50 (0 min) to 30/70 (50 minutes)
Flow rate: 1.0 mL/min
Detector: UV 230 nm
Injection amount: 10 μL
Analysis time: 50 minutes
The retention time under the above-mentioned conditions is 20.7 minutes.

Next, methods of measuring an ammonium ion content and calculating a conversion rate will be described, respectively.

Test Method 1: Measurement of Ammonium Ion Content

Standard solutions i to iv were analyzed using the analysis method shown below in a) and calibration curves were made. Sample solutions were analyzed and ammonium ion contents in Compound (EM), Compound (E), and Compound (E') were determined, respectively, from the calibration curves. A preparation process b) of the standard solutions and a preparation process c) of the sample solutions are as described below.

a) Ion Chromatograph Analysis Conditions
Column: TSK-GEL IC-Cation (50×4.6 mm i.d.)
Eluting solution: 2 mmol/L nitric acid
Injection amount: 100 μL
Flow rate: 1.2 mL/min
Oven: 30° C.
Polarity: −
Response: 1.0 second b) Preparation of Standard Solutions After 100 mg of ammonium chloride was weighed, purified water was added thereto to make the whole volume 100 mL (standard solution i). After 1 mL of the resulting standard solution i was weighed, a mixed solution of methanol and water was added thereto to make the whole volume 100 mL (standard solution ii). After 10 mL of the to resulting standard solution ii was weighed, a mixed solution of methanol and water was added thereto to make the whole volume 100 mL (standard solution iii). After 10 mL of the resulting standard solution iii was weighed, a mixed solution of methanol and water was added thereto to make the whole volume 100 mL (standard solution iv).

c) Preparation of Sample Solutions

After 20 mg of each of Compound (EM), Compound (E), and Compound (E') was weighed, a mixed solution of methanol and water was added thereto to make the whole volume 20 ml. The resulting solution was used as a sample solution.

Test Method 2: Calculation Method of Conversion Rate $$\text{Conversion Rate} = \frac{A_{FK}}{A_{FK} + A_{(EM,\ E,\ or\ E')}} \times 100 \quad \text{[Equation 1]}$$

In the above equation, A represents a peak area of each compound in HPLC using the below-described method;
$A_{FK}$ represents a peak area of Compound (FK);
$A_{EM}$ represents a peak area of Compound (EM);
$A_E$ represents a peak area of Compound (E); and
$A_{E'}$ represents a peak area of Compound (E').

HPLC Conditions
Column: YMC-Pack ODS-AQ (length: 25 cm, inner diameter: 4.6 mm, particle size: 3 μm, YMC)
Column temperature: 25° C.
Mobile phase: 10 mM aqueous potassium dihydrogen phosphate solution/acetonitrile=55/45
Flow rate: 0.7 mL/min
Detector: UV 230 nm
Injection amount: 5 μL
Analysis time: 40 minutes Example 7

Study on Reproducibility of Conversion Rate (Reaction Efficiency)

The following experiment has revealed by using, for example, Compound (E) the to reason why a reaction for preparing Compound (FK) from the unpurified Compound (EM), Compound (E), or Compound (E') does not achieve a conversion rate (reaction efficiency) with reproducibility.

Experiment of Cause Investigation 1

Addition of Expected Impurity into Compound (E)

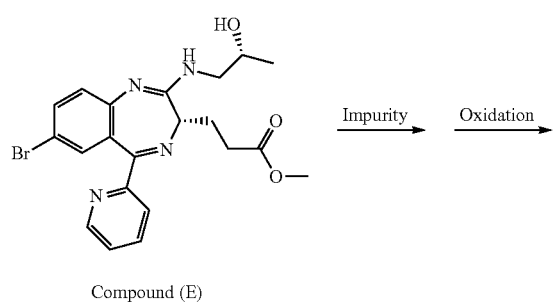

Compound (E)

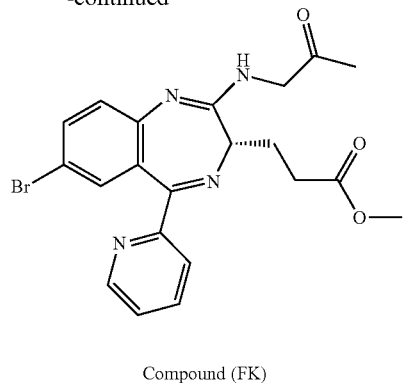

Compound (FK)

Experiment of Cause Investigation 1-1

Addition of Ammonium Chloride

Ammonium chloride (2.0 mg, 0.038 mmol, weight ratio relative to Compound (E): 2000 ppm) was added to Compound (E) in a mixed solvent of 7.5 mL of methyl acetate, 12.5 mL of toluene, and 0.1 mL of water. At 0° C., 13 mg of potassium bromide (0.11 mmol), an aqueous solution of sodium hydrogen carbonate (4 mL, 7.7 wt %), and 0.99 mg of AZADO (0.0065 mmol) were added to the reaction mixture. At 0° C., 1.6 g of an aqueous solution of sodium hypochlorite (2.6 mmol, 12.3 wt %) was added to the reaction mixture. After stirring for one hour, a conversion rate of the reaction mixture was determined by the above-mentioned test method 2.

Experiment of Cause Investigation 1-2

Addition of (R)-1-aminopropan-2-ol

An operation similar to that of Experiment of cause investigation 1-1 except that ammonium chloride (2.0 mg) was replaced by the same weight of (R)-1-aminopropan-2-ol (2.0 mg) was conducted and a conversion rate was determined using the above-mentioned test method 2.

Experiment of Cause Investigation 1-3

No Addition

An operation similar to that of Experiment of cause investigation 1-1 was conducted without adding ammonium chloride instead of adding ammonium chloride (2.0 mg) and a conversion rate was determined using the above-mentioned test method 2.

The results of the experiment of cause investigation 1 are shown below in Table 1. It has been found from Table 1 that when no ammonium chloride was added (Experiment of cause investigation 1-3) and when (R)-1-aminopropan-2-ol was added (Experiment of cause investigation 1-2), the oxidation reaction proceeded without a problem, a conversion rate was as high as 99.9%, and the reaction efficiency was good. When ammonium chloride was added (Experiment of cause investigation 1-1), on the other hand, the conversion rate of the oxidation reaction was 78.5% and the reaction efficiency was not quite satisfactory.

TABLE 1

| Experiment of cause investigation 1 | Addition or no addition of impurity | Conversion rate of oxidation reaction |
|---|---|---|
| 1-1 | Addition of ammonium chloride | 78.5% |
| 1-2 | Addition of (R)-1-aminopropan-2-ol | 99.9% |
| 1-3 | No addition | 99.9% |

Experiment of Cause Investigation 2

Addition of Ammonium Chloride Analog into Compound (E)

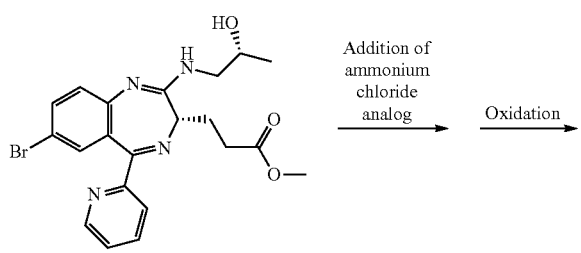

Compound (E)

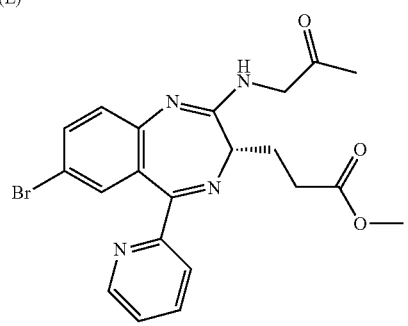

Compound (FK)

Experiment of Cause Investigation 2-1

Addition of Ammonium Chloride

Ammonium chloride (2.0 mg, 0.038 mmol) was added to Compound (E) (1.0 g, 2.2 mmol) in a mixed solvent of 7.5 mL of methyl acetate, 12.5 mL of toluene, and 0.1 mL of water. At 0° C., 13 mg of potassium bromide (0.11 mmol), an aqueous solution of sodium hydrogen carbonate (4 mL, 7.7 wt %), and 0.99 mg of AZADO (0.0065 mmol) were added to the reaction mixture. At 0° C., 1.6 g of an aqueous solution of sodium hypochlorite (2.6 mmol, 12.3 wt %) was added to the reaction mixture. After stirring for one hour, a conversion rate of the reaction mixture was determined using the above-mentioned test method 2.

Experiment of Cause Investigation 2-2

Addition of Ammonium Bromide

An operation similar to that of Experiment of cause investigation 2-1 except that ammonium chloride (0.038 mmol) was replaced by the same molar amount of ammonium bromide (3.7 mg, 0.038 mmol) was conducted and a conversion rate was determined using the above-mentioned test method 2.

Experiment of Cause Investigation 2-3

Addition of Ammonium Acetate

An operation similar to that of Experiment of cause investigation 2-1 except that ammonium chloride (0.038 mmol) was replaced by the same molar amount of ammonium acetate (2.9 mg, 0.038 mmol) was conducted and a conversion rate was determined using the above-mentioned test method 2.

Experiment of Cause Investigation 2-4

Addition of Ammonium Carbonate

An operation similar to that of Experiment of cause investigation 2-1 except that ammonium chloride (0.038 mmol) was replaced with the same molar amount of ammonium carbonate (3.6 mg, 0.038 mmol) was conducted and a conversion rate was determined using the above-mentioned test method 2.

Experiment of Cause Investigation 2-5

Addition of Aqueous Ammonia Solution

An operation similar to that of Experiment of cause investigation 2-1 except that ammonium chloride (0.038 mmol) was replaced by the same molar amount of a 28 wt % aqueous ammonia solution (2.3 mL, 0.038 mmol) was conducted and a conversion rate was determined using the above-mentioned test method 2.

Experiment of Cause Investigation 2-6

Addition of Sodium Chloride

An operation similar to that of Experiment of cause investigation 2-1 except that ammonium chloride (0.038 mmol) was replaced by the same molar amount of sodium chloride (2.2 mg, 0.038 mmol) was conducted and a conversion rate was determined using the above-mentioned test method 2.

Experiment of Cause Investigation 2-7

Addition of Hydrochloric Acid

An operation similar to that of Experiment of cause investigation 2-1 except that ammonium chloride (0.038 mmol) was replaced by the same molar amount of 6 mol/L hydrochloric acid (0.0063 mL, 0.038 mmol) was conducted and a conversion rate was determined using the above-mentioned test method 2.

Experiment of Cause Investigation 2-8

Addition of Tetrabutylammonium Bromide

An operation similar to that of Experiment of cause investigation 2-1 except that ammonium chloride (0.038 mmol) was replaced by the same molar amount of tetrabutylammonium bromide (12.1 mg, 0.038 mmol) was conducted and a conversion rate was determined using the above-mentioned test method 2.

The results of the experiment of cause investigation 2 are shown below in Table 2. It has been found from Table 2 that in Experiments of cause investigation 2-6 and 2-7, the oxidation reaction proceeded without a problem, the conversion rate was as high as about 99% or more, and the reaction efficiency was good, suggesting that the chloride ion of ammonium chloride is not a substance impeding the oxidation reaction. In Experiments of cause investigation 2-2, 2-3, 2-4, and 2-5, on the other hand, the conversion rate of the oxidation reaction was from about 30 to 60% and the reaction efficiency was much inferior, suggesting that the ammonium ion of ammonium chloride was presumed to be a substance impeding the oxidation reaction. In Experiment of cause investigation 2-8 in which a tetrabutylammonium ion, that is, the same cation as the ammonium ion was added, the oxidation reaction proceeded without a problem. From these findings, a substance impeding the efficient progress of the oxidation reaction was strongly presumed to be an ammonium ion.

TABLE 2

| Experiment of cause investigation 2 | Addition of ammonium chloride analog | Conversion rate of oxidation reaction |
|---|---|---|
| 2-1 | Ammonium chloride | 78.5% |
| 2-2 | Ammonium bromide | 37.3% |
| 2-3 | Ammonium acetate | 29.9% |
| 2-4 | Ammonium carbonate | 59.8% |
| 2-5 | Aqueous ammonia solution | 55.8% |
| 2-6 | Sodium chloride | 99.9% |
| 2-7 | Hydrochloric acid | 98.9% |
| 2-8 | Tetrabutylammonium bromide | 98.2% |

Based on the above-mentioned results of Experiments of cause investigation 1 and 2, Experiment 3 was conducted to find a correlation between an ammonium ion content and a conversion rate from Compound (E) to Compound (FK).

Experiment 3

Experiment on Correlation Between Ammonium Ion Content and Conversion Rate

Compound (FK) was prepared by an operation similar to that of Example 3 by using Compound (E) different in lot whose ammonium content had been determined using the above-mentioned test method 1, a conversion rate was calculated using the test method 2, and a correlation between an ammonium ion content and a conversion rate was found. The ammonium ion content and a conversion rate of each lot are as shown below in Table 3. Incidentally, for example, an ammonium ion content of 20 ppm in the Experiment 3-1 means that an ammonium ion content is 20 µg relative to 1 g of Compound (E).

TABLE 3

| Experiment 3 (Lot No.) | Ammonium ion content (ppm) | Conversion rate of oxidation reaction (%) |
|---|---|---|
| 3-1 | 20 | 100 |
| 3-2 | 74 | 98.4 |
| 3-3 | 130 | 99.0 |
| 3-4 | 163 | 98.0 |
| 3-5 | 211 | 94.5 |
| 3-6 | 221 | 94.3 |
| 3-7 | 243 | 92.6 |
| 3-8 | 272 | 95.7 |

It has been found from the above results that when Compound (E) having an ammonium ion content of about 200 ppm or more is used as a raw material of an oxidation reaction, a conversion rate of the oxidation reaction varies and the oxidation reaction is not stable. It has also been found that when Compound (E) having an ammonium ion content of about 170 ppm or less is used as a raw material of an oxidation reaction, on the other hand, a conversion rate of the oxidation reaction is 98% or more and the oxidation reaction is stable with good reproducibility.

FIG. 1 shows these results as a graph.

Figure 2:
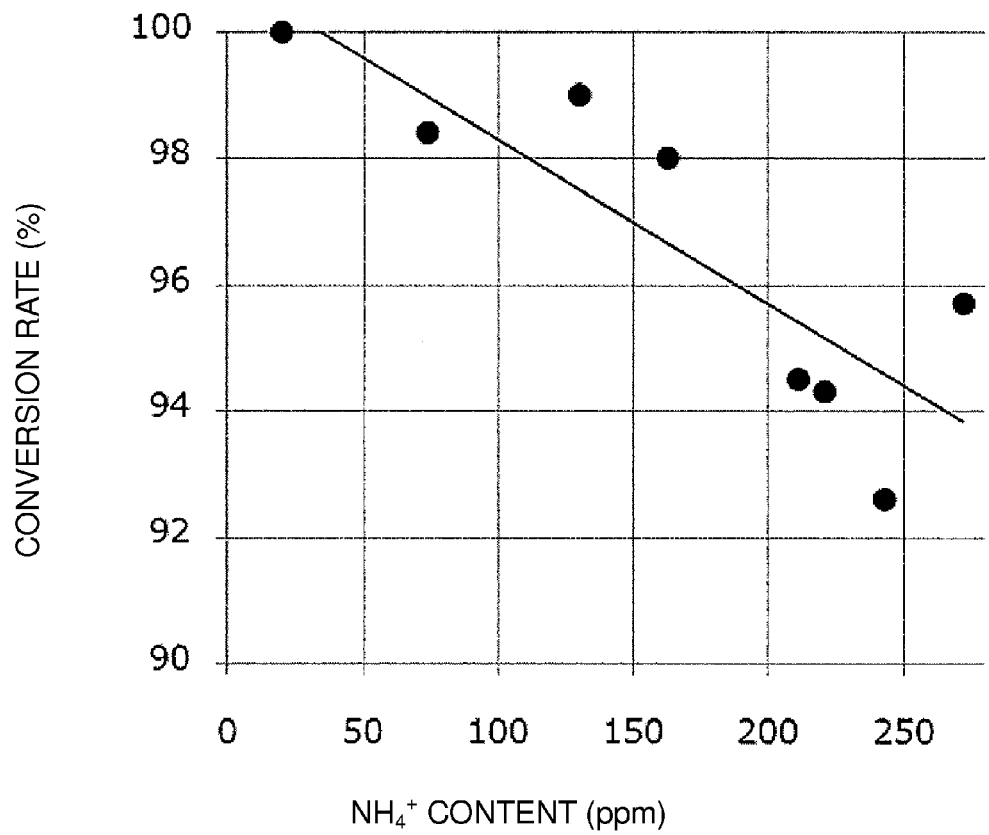
FIG. 2 is a graph showing both the graph of FIG. 1 and an approximate curve (linear approximation).

FIG. 2 shows both the results of FIG. 1 and an approximate curve (linear approximation). Although a negative relation can be found between an ammonium ion content and a conversion rate from Compound (E) to Compound (FK), it is preferred to understand that the approximate curve (linear approximation) shown in this graph is only one example because there are various ways how to find an approximate curve. The following was the equation of the approximate curve in the graph: [conversion rate (%)=−0.0258 (NH$_4^+$ content (ppm)+100.87)].

INDUSTRIAL APPLICABILITY

According to the present invention, Compound (FK) can be prepared at a markedly high conversion rate and/or oxidation catalyst efficiency with good reproducibility from a compound selected from the group consisting of Compound (EM), Compound (E), and Compound (E'), even if it is an unpurified compound. Compound (FK) is an important synthesis intermediate of Compound (P) having sedative and anesthetic actions. Since the preparation process of the present invention can stably supply Compound (FK) with good reproducibility without conducting a particular purification step, it is very useful from the standpoint of industrial productivity of Compound (P) which is an active pharmaceutical ingredient.

The invention claimed is:
1. A process for preparing 3-[(S)-7-bromo-2-((2-oxopropyl)amino)-5-pyridin-2-yl-3H-1,4-benzodiazepin-3-yl]propionic acid methyl ester represented by the formula:

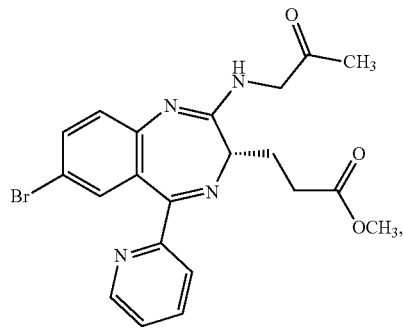 [SMILES: COC(=O)CC[C@@H]1N=C(c2ccccn2)c2cc(Br)ccc2N=C1NCC(C)=O]

comprising:
oxidizing a compound selected from the group consisting of 3-[(S)-7-bromo-2-((2-hydroxypropyl)amino)-5-pyridin-2-yl-3H-benzo[e][1,4]diazepin-3-yl]propionic acid methyl ester, 3-[(S)-7-bromo-2-(((R)-2-hydroxypropyl)amino)-5-pyridin-2-yl-3H-benzo[e][1,4]diazepin-3-yl]propionic acid methyl ester and 3-[(S)-7-bromo-2-(((S)-2-hydroxypropyl)amino)-5-pyridin-2-yl-3H-benzo[e][1,4]diazepin-3-yl]propionic acid methyl ester in the presence of at least one oxidation catalyst selected from the group consisting of:
(i) 2,2,6,6-tetramethylpiperidin-1-ol;
(ii) 2,2,6,6-tetramethylpiperidine-1,4-diol; and
(iii) a compound represented by the formula (I-1):

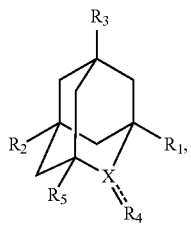

(I-1)

wherein:
R₁, R₂ and R₅ independently represent hydrogen, halogen, hydroxy, $C_{1-3}$ alkyl or $C_{1-3}$ alkoxy;
R₃ represents hydrogen or halogen; and

X⚌R₄ represents N—O·, N—OH or N⁺═O;
wherein the oxidation of the compound selected from the group consisting of 3-[(S)-7-bromo-2-((2-hydroxypropyl)amino)-5-pyridin-2-yl-3H-benzo[e][1,4]diazepin-3-yl]propionic acid methyl ester, 3-[(S)-7-bromo-2-(((R)-2-hydroxypropyl)amino)-5-pyridin-2-yl-3H-benzo[e][1,4]diazepin-3-yl]propionic acid methyl ester and 3-[(S)-7-bromo-2-(((S)-2-hydroxypropyl)amino)-5-pyridin-2-yl-3H-benzo[e][1,4]diazepin-3-yl]propionic acid methyl ester is conducted in a reaction system satisfying at least one of the following conditions (a), (b) and (c):
(a) in the absence of an ammonium ion;
(b) in the presence of an ammonium ion in a weight ratio of 170 ppm or less relative to the compound; and
(c) in the presence of an ammonium ion in a molar ratio of 145% or less relative to the oxidation catalyst.

2. The process according to claim 1, wherein the compound selected from the group consisting of 3-[(S)-7-bromo-2-((2-hydroxypropyl)amino)-5-pyridin-2-yl-3H-benzo[e][1,4]diazepin-3-yl]propionic acid methyl ester, 3-[(S)-7-bromo-2-(((R)-2-hydroxypropyl)amino)-5-pyridin-2-yl-3H-benzo[e][1,4]diazepin-3-yl]propionic acid methyl ester and 3-[(S)-7-bromo-2-(((S)-2-hydroxypropyl)amino)-5-pyridin-2-yl-3H-benzo[e][1,4]diazepin-3-yl]propionic acid methyl ester is unpurified prior to the oxidation.

3. The process according to claim 1, wherein the oxidation catalyst is 2-azaadamantane-N-oxyl or 2-azaadamantane-2-ol.

4. The process according to claim 1, wherein the oxidation is conducted at a conversion rate of 98% or more.

5. The process according to claim 2, wherein the oxidation is conducted at a conversion rate of 98% or more.

* * * * *

UNITED STATES PATENT AND TRADEMARK OFFICE
CERTIFICATE OF CORRECTION

PATENT NO. : 9,656,987 B2
APPLICATION NO. : 14/772203
DATED : May 23, 2017
INVENTOR(S) : Yuji Kawakami et al.

It is certified that error appears in the above-identified patent and that said Letters Patent is hereby corrected as shown below:

In the Specification

In Column 1, Line 23, delete "-benzo[1,4]" and insert -- -benzo[e][1,4] --, therefor.

In Column 18, Lines 46-47, delete "3-[(S)-7-bromo-2-((R)-2-((R)-2-hydroxy-proxy-propylamino)-5-pyridin-2-yl-3H-benzo[e][1,4]diazepin-3-yl]propionic acid methyl ester" and insert -- 3-[(S)-7-bromo-2-((R)-2-hydroxy-propylamino) -5-pyridin-2-yl-3H-benzo[e][1,4]diazepin-3-yl]propionic acid methyl ester --, therefor.

In Column 23, Lines 58-64, delete " 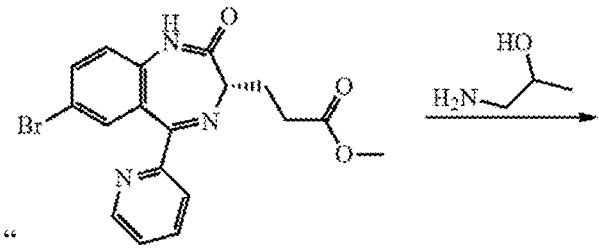 " and insert -- 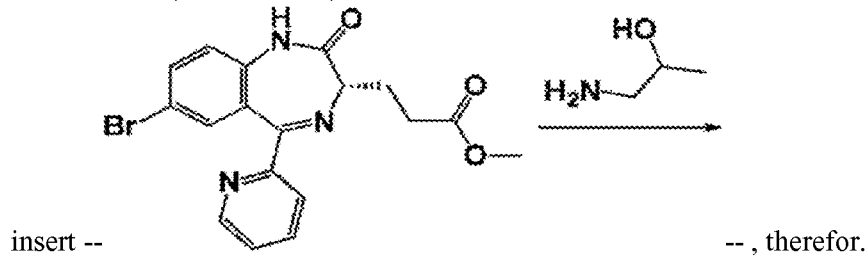 --, therefor.

Signed and Sealed this
Eighth Day of May, 2018

Andrei Iancu
*Director of the United States Patent and Trademark Office*

CERTIFICATE OF CORRECTION (continued)
U.S. Pat. No. 9,656,987 B2

In Column 26, Lines 57-64, delete " 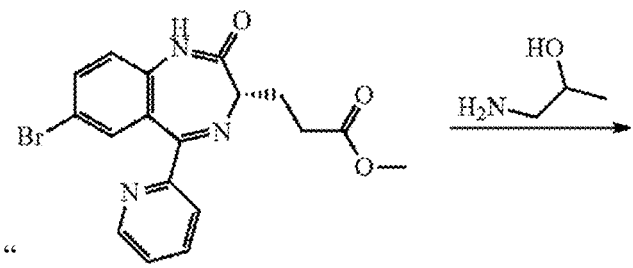 " and insert -- 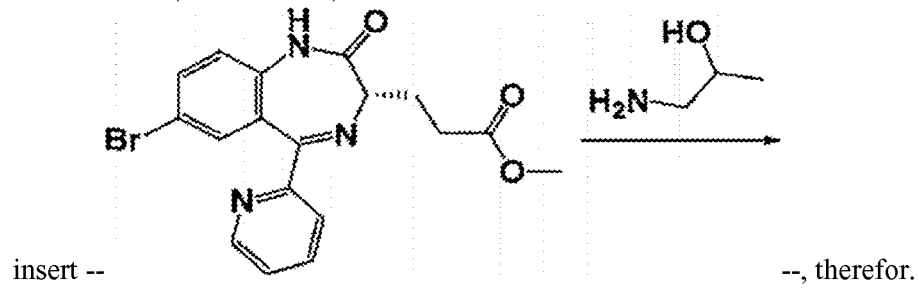 --, therefor.